(12) United States Patent
Xiao et al.

(10) Patent No.: US 12,280,154 B2
(45) Date of Patent: Apr. 22, 2025

(54) COLONIC MICROBIOTA RESPONSIVE POLYMER AND ITS PREPARATION METHOD AND USE

(71) Applicant: Shanghai Jiaotong University School of Medicine, Shanghai (CN)

(72) Inventors: Zeyu Xiao, Shanghai (CN); Gaoxian Chen, Shanghai (CN); Kai Cui, Shanghai (CN)

(73) Assignee: SHANGHAI JIAOTONG UNIVERSITY SCHOOL OF MEDICINE, Shanghai (CN)

( * ) Notice: Subject to any disclaimer, the term of this patent is extended or adjusted under 35 U.S.C. 154(b) by 0 days.

(21) Appl. No.: 18/474,990

(22) Filed: Sep. 26, 2023

(65) Prior Publication Data

US 2024/0165037 A1 May 23, 2024

(30) Foreign Application Priority Data

Oct. 27, 2022 (CN) .......................... 202211329338.2

(51) Int. Cl.
| | |
|---|---|
| A61K 47/14 | (2017.01) |
| A61K 9/48 | (2006.01) |
| A61P 1/00 | (2006.01) |
| C08B 37/00 | (2006.01) |

(52) U.S. Cl.
CPC .............. *A61K 9/4816* (2013.01); *A61P 1/00* (2018.01); *C08B 37/0006* (2013.01)

(58) Field of Classification Search
CPC ... A61P 1/00; C08B 37/0006; C08B 37/0012; A61K 47/14
See application file for complete search history.

(56) References Cited

FOREIGN PATENT DOCUMENTS

CN 108401418 A 8/2018

OTHER PUBLICATIONS

Choi, et al: "A novel polycondensate containin cyclodextrin and lactose: Synthesis, metal-complexing properties, and degradation", Polymer 48, 2007, pp. 1445-1449.

(Continued)

*Primary Examiner* — San Ming R Hui
(74) *Attorney, Agent, or Firm* — FOX ROTHSCHILD LLP

(57) ABSTRACT

The invention provides a colonic microbiota responsive polymer characterized in that it is prepared by the polymerization of a response monomer and a linking monomer, wherein the response monomer is a cellobiose with a β-(1,4)-glucoside bond or/and a lactose with a β-galactoside bond; the linking monomer is a monomer that reacts with the hydroxyl group of the response monomer to form an ester or ether directly or by a crosslinking agent. The invention also provides a method for preparation of a colonic microbiota responsive polymer, a degradable film based on the polymer and a preparation method thereof. By means of the characteristics that β-(1,4)-glucoside bond provided by cellobiose or/and β-galactoside bond provided by lactose monomer unit in the polymer can specifically respond to the high abundance of microbiotas (β-glucosidase or/and β-galactosidase) in the colon to specifically degrade in the colon, a colon-targeted delivery system for diagnosis and treatment of colon diseases is constructed.

14 Claims, 18 Drawing Sheets

(56) References Cited

OTHER PUBLICATIONS

Shown, et al: "Synthesis and Characterization of Linear Water-soluble gamma-Cyclodextrin based Polymers as Drug Carrier Systems", Supramolecular Chemistry, Sep. 2008, vol. 20 (6), pp. 573-578.
Fischer, et al: "Assessment of Small Intestinal Transit Times in Ulcerative Colitis and Crohn's Disease Patients with Different Disease Activity Using Video Capsule Endoscopy", AAPS Pharmscitech Feb. 2017, vol. 18, No. 2, pp. 404-409, doi: 10.1208/s12249-016-0521-3.
Morales-Burgos, et al: "Tailoring reversible insulin aggregates loaded in electrosprayed arabinoxylan microspheres intended for colon-targeted delivery", Journal of Applied Polymer Science, May 16, 2019, 136, 47960, DOI: 10.1002/app.47960.
Zhang, et al: "A superoxide dismutase/catalase mimetic nanomedicine for targeted therapy of inflammatory bowel disease", Biomaterials, Oct. 2016, 105, pp. 206-221, doi: 10.1016/j.biomaterials.2016.08.010.
Zhu, et al: "Preparation and characterization of pectin/chitosan beads containing porous starch embedded with doxorubicin hydrochloride: A novel and simple colon targeted drug delivery system", Food Hydrocolloid, 2019, 95, pp. 562-570.
First Office Action dated Jun. 19, 2023 issued in Chinese Patent Application No. 202211329338.2 (12 pages).
English translation of First Office Action dated Jun. 19, 2023 issued in Chinese Patent Application No. 202211329338.2 (9 pages).
Second Office Action dated Jan. 10, 2024 issued in Chinese Patent Application No. 202211329338.2 (11 pages).
English translation of Second Office Action dated Jan. 10, 2024 issued in Chinese Patent Application No. 202211329338.2 (14 pages).

COLONIC MICROBIOTA RESPONSIVE POLYMER AND ITS PREPARATION METHOD AND USE

TECHNICAL FIELD

The invention relates to the field of pharmaceutical preparations and the technical field of polymer chemistry, in particular to a polymer that is stable in form and responds to the high abundance of β-glucosidase or/and β-galactosidase in the colon and a film thereof, a preparation method thereof and its application in colon-target delivery system.

BACKGROUND ART

Bioresponsive polymer materials are an important field of biomaterials, which aim to achieve the responsive release of the drugs encapsulated in the site of diseases, to improve the availability of drugs and to reduce the toxic side effects of the systemic distribution of drugs on normal tissues.

The existing research on bioresponsive polymer materials is mainly focused on pH (Kocak et al., 2017, Pang et al., 2016) and redox (Zhang et al., 2017, Fukino et al., 2017) response fields. Since the 1980s, a large number of related patents have reported on these two types of materials, and some common responsive materials such as hydroxypropyl methyl cellulose phthalates have been included in the pharmacopoeia. Hydroxypropyl methylcellulose phthalate (HPMCP), hydroxypropyl methylcellulose acetate succinate (HPMCAS) and cellulose acetate phthalate (CAP) have all been industrialized. However, the response mechanism of these materials is lack of disease tissue specificity, which limits their application.

In contrast, a large number of colonic bacteria enzymes exist in the organism provide a large number of stimulators for bioresponsive materials, and their specificity for disease tissues will be much higher than pH or redox response (Hu et al., 2014). However, the commonly used colon microbiota responsive polymer materials [such as sodium alginate (Dong et al., 2010), chitosan (Cai et al., 2020), guar gum, etc.] face the problem of low specificity of colon response. This is because that these polymer materials can also trigger their degradation under the stimulation of acid and alkaline environment of stomach, small intestine and colon; at the same time, there are a variety of enzyme response units in such polymer structure (e.g. response units for enzymes in the small intestine), resulting in low specificity of the response to microbiotas in the colon. Finally, the oral colon-target delivery system designed with these polymer materials will face the problem of early leakage and release in the stomach or small intestine, resulting in low efficiency of colon specific release and limited availability of delivered diagnostic or therapeutic reagents in the colon.

Therefore, it is urgent to develop a polymer material that responds to highly specific colon microbiotas and is stable in acid and alkaline environment to design a colon-target delivery system so as to ensure that the delivered diagnostic or therapeutic reagents will not leak in advance due to the complex acid and alkaline environment and enzyme environment in the stomach and small intestine in the digestive system before reaching the colon, and reduce the side effects caused by early leakage in order to improve the release rate of diagnostic or therapeutic reagents in the colon, and finally enhance the diagnostic sensitivity and drug treatment effect.

SUMMARY OF THE INVENTION

The inventor has found and confirmed through high-throughput colonic microflora screening analysis and experimental studies that β-glucosidase and β-galactosidase are the microbiotas with the highest abundance and colon specificity in colon environment, and their abundance is significantly higher than that of azo reductase responding to the stimulation of commonly used microbiota responsive polymer materials. Therefore, β-glucosidase and β-galactosidase are the most promising stimulus responders of polymers used to construct colon-target delivery system. In order to obtain a polymer that is stable under gastrointestinal acid-base conditions and responds to the stimulation of the above two colonic bacteria enzymes, and thereby construct a colon-target delivery system, the inventors selected cellobiose with a β-(1,4)-glucoside bond or/and a lactose with a β-galactoside bond as response monomers to assist the polymerization of the linking monomers with stability in the gastrointestinal acid-base environment. The obtained polymer has an ability of specific response to colon microbiotas (β-glucosidase and β-galactosidase) and a stability in the gastrointestinal acid-base environment, thereby ensuring that the colon-target delivery system constructed with the polymer will not leak the drugs or imaging agents carried in the gastrointestinal site due to changes in the acid-base environment.

Therefore, it is an object of the present invention to provide a colonic microbiota responsive polymer. The microbiota responsive polymer can realize: 1) specific response to the high abundance of microbiotas (β-glucosidase and β-galactosidase) in colon; and optionally 2) stability in the gastrointestinal acid-base environment, thereby ensuring that the colonic microbiota responsive polymer does not degrade in the gastrointestinal tract environment with different acid-base environments alone or together with other auxiliary technical means, and then constructing a colon-target delivery system based on the colon specific microbiota responsive polymer.

To achieve the above purposes, the invention provides a colonic microbiota responsive polymer. The polymer responds to the high abundance of microbiotas β-glucosidase and β-galactosidase) in colon and degrades, and thereby can be used to construct a colon-target delivery system. The structural feature of the polymer is that the colonic microbiota responsive structural unit contained therein is cellobiose or/and lactose, which can be specifically degraded by β-glucosidase or/and β-galactosidase, respectively.

The technical solution of the colonic microbiota responsive polymer of the invention is:

A colonic microbiota responsive polymer characterized in that it is prepared by the polymerization of a response monomer and a linking monomer, wherein the response monomer is a cellobiose with a β-(1,4)-glucoside bond or/and a lactose with a β-galactoside bond; the linking monomer is a monomer that reacts with the hydroxyl group of the response monomer to form an ester or ether directly or by a crosslinking agent.

The β-(1,4)-glucoside bond of the cellobiose aor/and the β-galactoside bond of the lactose in the polymer break under the action of β-glucosidase or β-galactosidase, leading to the degradation of the polymer.

According to one embodiment of the invention, it is characterized in that the polymer responds to the high abundance of β-glucosidase and/or β-galactosidase in colon and degrades, and thereby the diagnostic or therapeutic reagents encapsulated in the film-forming polymer can be specifically released in the colon.

According to one embodiment of the invention, it is characterized in that the linking monomer is stable in the gastrointestinal acid-base environment. The linking monomer is selected from one or more of the group consisting of γ-cyclodextrin, β-cyclodextrin, hydroxypropyl-β-cyclodextrin, acrylates (such as methyl acrylate, ethyl acrylate, propyl acrylate), hydroxyacrylic acid, preferably β-cyclodextrin.

According to one embodiment of the invention, it is characterized in that a single or multiple response monomer units are connected with a single or multiple linking units directly or by a cross-linking agent to form homopolymers, copolymers, block copolymers or random copolymers.

According to one embodiment of the invention, it is characterized in that the polymerization degree of the response monomer is 20~80, such as 30~40; the polymerization degree of the linking monomer is 20~50, such as 20~30.

According to one embodiment of the invention, it is characterized in that the feeding mass ratio of the response monomer and the linking monomer in the polymerization process is not less than 1:5. thereby ensuring that sufficient response monomer units interact with the above colonic microbiota so that the drugs are fully released.

According to one embodiment of the invention, the polymerization is carried out in the presence of a crosslinking agent selected from one or more of the group consisting of epichlorohydrin, hydroquinone dihydroxyethyl ether, disuccinimidylsuberate and Sulfo-SMCC; preferably, the crosslinking agent is epichlorohydrin.

In one embodiment of the invention,

The polymer of the invention comprises β-cyclodextrin linking monomer units and cellobiose monomer units, and the linking structure can be expressed by, but not limited to, the following structural formula:

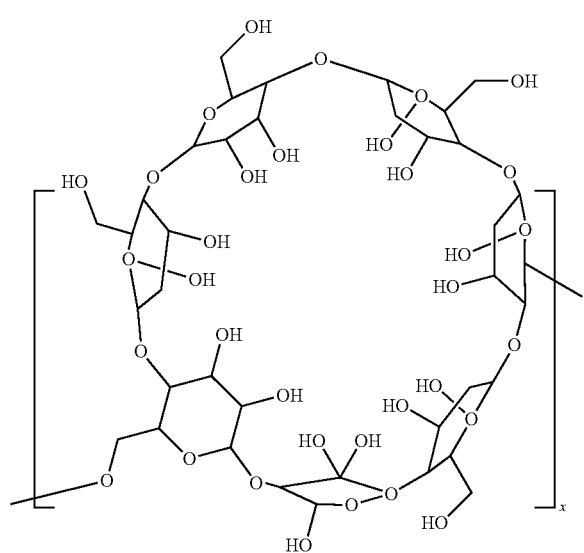

wherein x and y independently represent the total polymerization degree of β-cyclodextrin linking monomer units and cellobiose monomer units in the polymer, x is 20~50, e.g., 20~30, y is 20~80, e.g., 30~40; wherein the single or multiple β-cyclodextrin linking monomer units can be connected with the single or multiple cellobiose monomer units directly or by a cross-linking agent to form different types of polymers, including homopolymers, copolymers, block copolymers or random copolymers. In case where a cross-linking agent is used, the polymer also comprises a cross-linking agent group formed between β-cyclodextrin linking monomer units and cellobiose monomer units.

The chemical structure of cellobiose response monomer is:

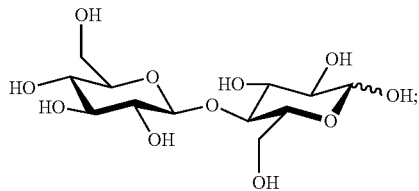

The chemical structure of lactose response monomer is:

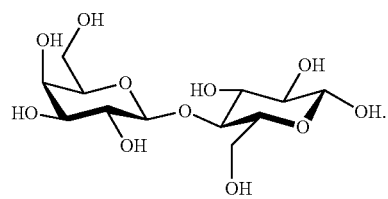

In one embodiment of the invention, the microbiota responsive polymer is stable under pH 4.0-8.0 environment and responds to β-glucosidase or/and β-galactosidase in this environment.

The invention also provides a preparation method of the microbiota responsive polymer.

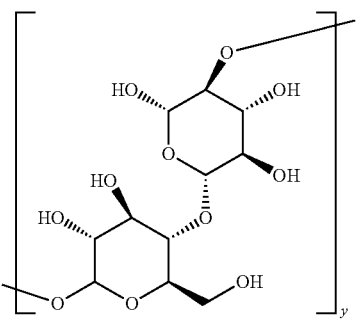

The cellobiose or lactose is used as the response monomer, to which the linking mononer is added. The linking monomer can be selected from, but not limited to, one or more of the group consisting of γ-cyclodextrin, β-cyclodextrin, hydroxypropyl-β-cyclodextrin, acrylates such as methyl acrylate, ethyl acrylate, propyl acrylate, or hydroxyacrylic acid.

The preparation method of the polymer of the invention is characterized in that, in an alkaline solution, for example, 5%-20% NaOH (w/v) alkaline solution, the response monomer and the linking monomer are polymerized especially under the protection of nitrogen, the polymerization can be carried out at room temperature, preferably at 40-60° C. It is preferable to react in the dark for a period of time, such as 12, 16, 20 and 24 hours.

According to one embodiment of the invention, the preparation method is carried out in the presence of a cross-linking agent, and the cross-linking agent is selected from one or more of the group consisting of epichlorohydrin, hydroquinone dihydroxyethyl ether, disuccinimidylsuberate and Sulfo-SMCC; preferably, the crosslinking agent is epichlorohydrin.

In one embodiment of the invention, the preparation method of microbiota responsive polymer is characterized in that, when the linking monomer is β-cyclodextrin, the feeding mass ratio of the response monomer to the linking monomer is not less than 1:5. In this way, it is guaranteed that more response monomer units in the microbiota responsive polymer interact with the microbiota. At the same time, the obtained polymer will have higher engineering strength, which is convenient for subsequent film forming applications.

The invention also provides a film of the polymer.

The polymer according to the invention can be prepared into β-glucosidase or/and β-galactosidase responsive polymer film. The polymer film can be coated on the surface of common dosage forms, including tablets, suppositories, capsules, microcapsules, drop pills and the like for resistance to the erosion of gastrointestinal environment, and degraded in response to the high abundance of microbiotas at the colon so as to specifically release diagnostic or therapeutic reagents.

The acid-base resistance of the polymer film of the invention can also be strengthened by virtue of a coat with stability in the gastrointestinal acid-base environment. For example, a pH-responsive layer (PL) resistant to gastric acid is coated outside the polymer film of the invention. The composition of PL layer can be a mixture of talcum powder, triethyl citrate and Eudragit 100 with a mass ratio of 1:1:1.5, wherein Eudragit 100 is a commercially available commodity for preparing pH responsive polymers.

The invention also provides a preparation method of the microbiota responsive polymer film.

In the preparation method of the microbiota responsive polymer film, it is necessary that the solution of the polymer obtained from any one of the above items is separately or mixed with pharmaceutically acceptable excipients, and then the polymer is solidified to form a film by phase transfer, solvent volatilization, chemical crosslinking, etc.

According to one embodiment of the invention, the pharmaceutically acceptable excipients are one or more of the group consisting of ethyl cellulose, hydroxypropyl methyl cellulose, chitosan, polyethylene glycol and polyvinyl alcohol. Polyvinyl alcohol is preferred.

In one embodiment of the invention, the preparation method of microbiota responsive polymer film is characterized in that the breaking strength of the prepared film is not less than 9 MPa.

The microbiota responsive polymer and a film thereof according to the invention can be used to construct a colon-target delivery system.

In the invention, the microbiota responsive polymer film can be used to coat diagnostic or therapeutic preparations. The preparations can be oral preparations, including but not limited to tablets, capsules, microcapsules, drop pills, or suppositories.

The invention also provides the use of the microbiota responsive polymer and the film thereof.

The colon-target delivery system constructed with the polymer and/or the polymer film of the invention is used for the diagnosis and treatment of diseases, such as colon diseases.

According to a typical embodiment of the invention, the microbiota responsive polymer film is prepared into an oral colon-target delivery capsule.

The use of the polymer and/or the polymer film of the invention in the preparation of a colon-target delivery system for diagnosis and/or treatment of diseases, such as capsules, and the diseases are for example colon diseases.

The subject of the colon-target delivery system of the invention is a mammal or a human.

The invention also provides a method for diagnosing and treating colon diseases of mammalian or human subjects, including administering the subject a colon-target delivery system constructed with the polymer and/or the polymer film of the invention, for example, a capsule coated with the polymer film of the invention.

EMBODIMENTS

The invention is described in detail with reference to the following specific examples and the drawings, but in any case, the protection scope of the invention is not limited by the specific examples.

Example 1

Preparation and Characterization of Colonic Microbiota Responsive Polymer

Figure 1:
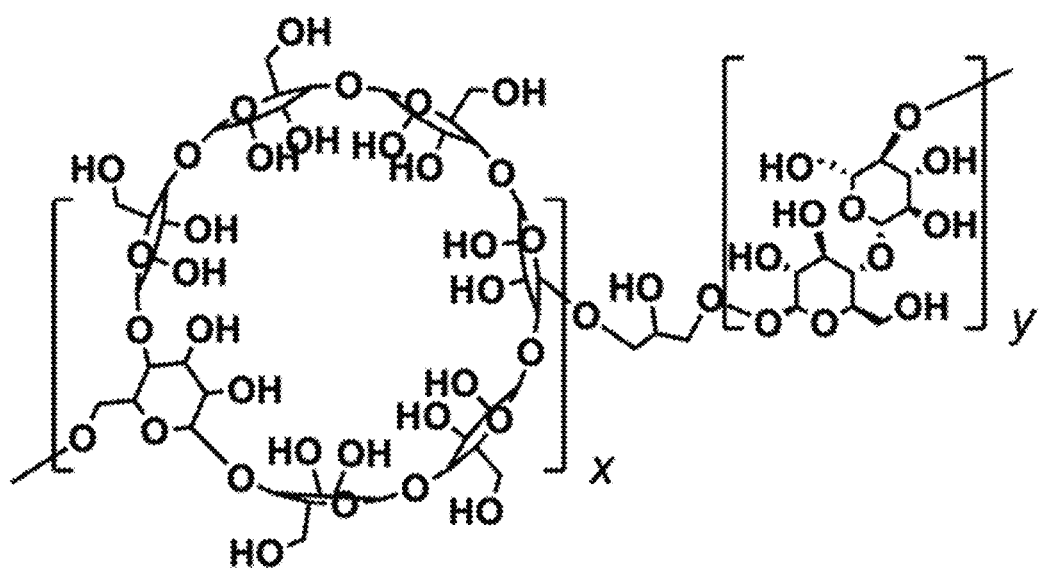
FIG. 1: is a diagram of the chemical structure of a microbiota responsive polymer of the invention.

In this example, cellobiose was used as the response monomer and β-cyclodextrin as a linking monomer. The inventors prepared a microbiota responsive polymer, and its structural unit was shown in FIG. 1.

Step 1: Synthesis of Colonic Microbiota Responsive Polymer

Ultrapure water and 4 mL of 20% NaOH solution (w/v) were added to 3.9 g β-cyclodextrin and 1 g cellobiose and dissolved with stirring as a polymer precursor solution. After complete dissolution, the reactor was placed in a water bath at 50° C., and 0.6 mL epichlorohydrin was added dropwise. After 24 hours, the excess epichlorohydrin was removed by dialysis. Then the resultant was freeze dried to obtain a yellowish gel product.

Step 2: Characterization of Colonic Microbiota Responsive Polymer

Figure 2:
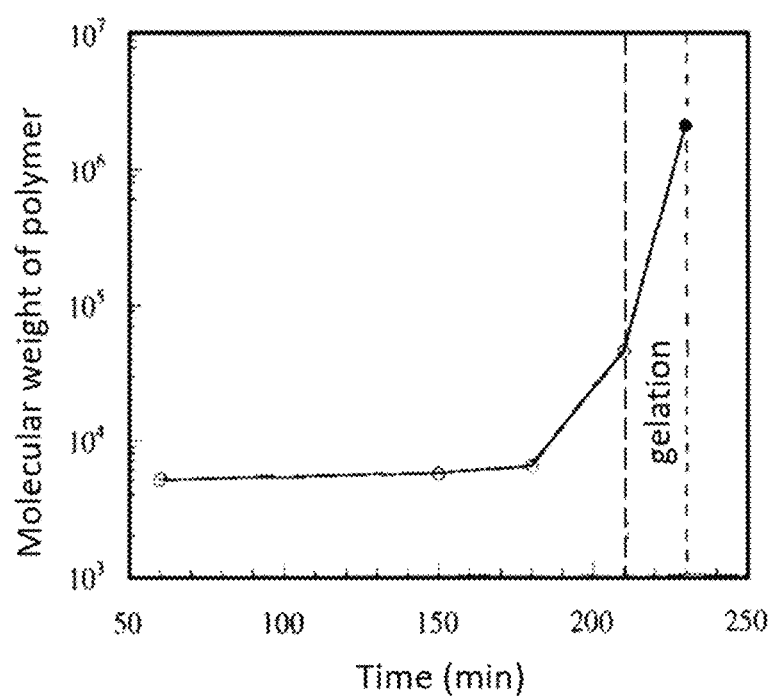
FIG. 2: shows the change of the molecular weight of microbiota responsive polymer with time.

Laser light scattering method was used to measure the average molecular weight of polymers. The three detection angles were 45", 90" and 135". The wavelength of the incident light was 690 nm. As the reaction time increased, the reactant presented a gel shape. According to the molecular weight distribution law reported by E. Renard et al., 1997, the molecular weight of the polymer shown in FIG. 2 was more than 400000, that is, the degree of polymerization x was 25 and y was 38.

Figure 3:
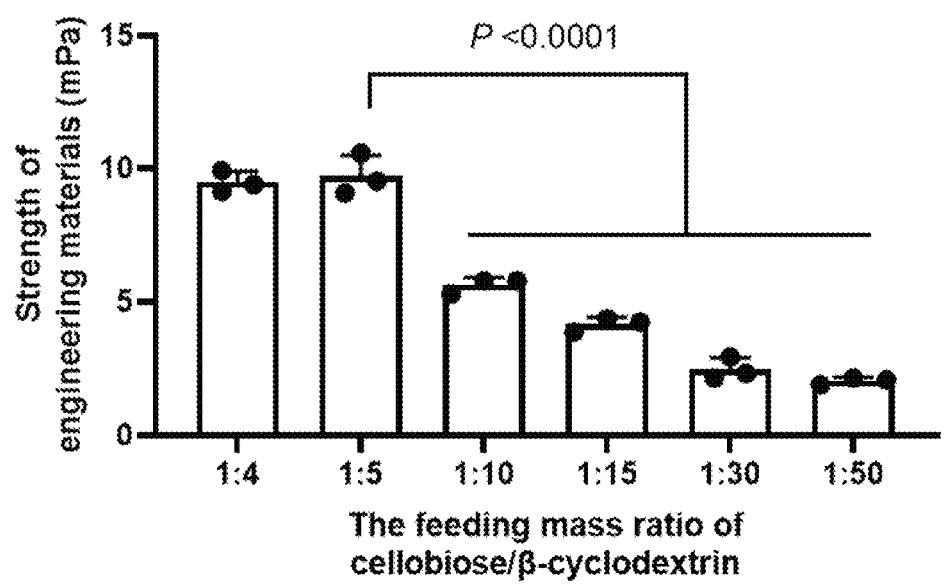
FIG. 3: shows the difference in mechanical strength of microbiota responsive polymer films prepared with different feeding ratios.

The inventors also studied the effect of the feeding ratio of cellobiose and cyclodextrin on the mechanical strength of the obtained polymer film, as shown in FIG. 3.

It can be seen from the comparison of the mechanical strength differences of the microbiota responsive polymer films prepared with different feed ratios that when the feed ratio of cellobiose to cyclodextrin was greater than 1:5, the polymer film exhibited strong mechanical strength, which was convenient for subsequent use as a coat. When the feed ratio of cellobiose to cyclodextrin was less than 1:5, the mechanical strength of the polymer film decreased significantly.

Example 2

Preparation and Performance Evaluation of Colonic Microbiota Responsive Polymer Film In this example, the polymer described in Example 1 was used to provide a method for preparing the film, and the acid-base stability and microbiota response specificity of the film were evaluated.

2.1: Preparation of Colonic Microbiota Responsive Polymer Film

The synthesized colonic microbiota responsive polymer was diluted to 1 g/mL in dimethyl sulfoxide (DMSO) as a precursor solution. The solution was mixed with 1 g/mL polyvinyl alcohol solution in 1:1 volume ratio, and then dried under vacuum at 65° C. overnight to form a film, which was dried to obtain the product.

2.2: Characterization of Films

The characterization of the films was verified by $^1$H-NMR. The sample was dissolved in 500 μL D$_2$O, and then transferred to an NMR tube. The $^1$H-NMR spectrum was measured with a 400 MHz nuclear magnetic resonance spectrometer at 298 K. The $^1$H-NMR spectrum was processed and analyzed using MestReNova software (v12.0.2).

The characteristic functional groups of the films were verified by Fourier Transform infrared spectroscopy (FTIR). In the sample preparation stage, a cross-linked film was formed on the glass slide and then freeze dried. Before detection, the film sample was scraped off the glass slide and placed on the surface of the potassium bromide slide for FTIR spectrum characterization. The FTIR spectrum was recorded in the form of transmitted light with a range of 7800~450 cm$^{-1}$ and a resolution of 8 cm$^{-1}$. Each pixel accumulated 160 spectra, which were recorded and analyzed with OMNIC software.

Figure 4:
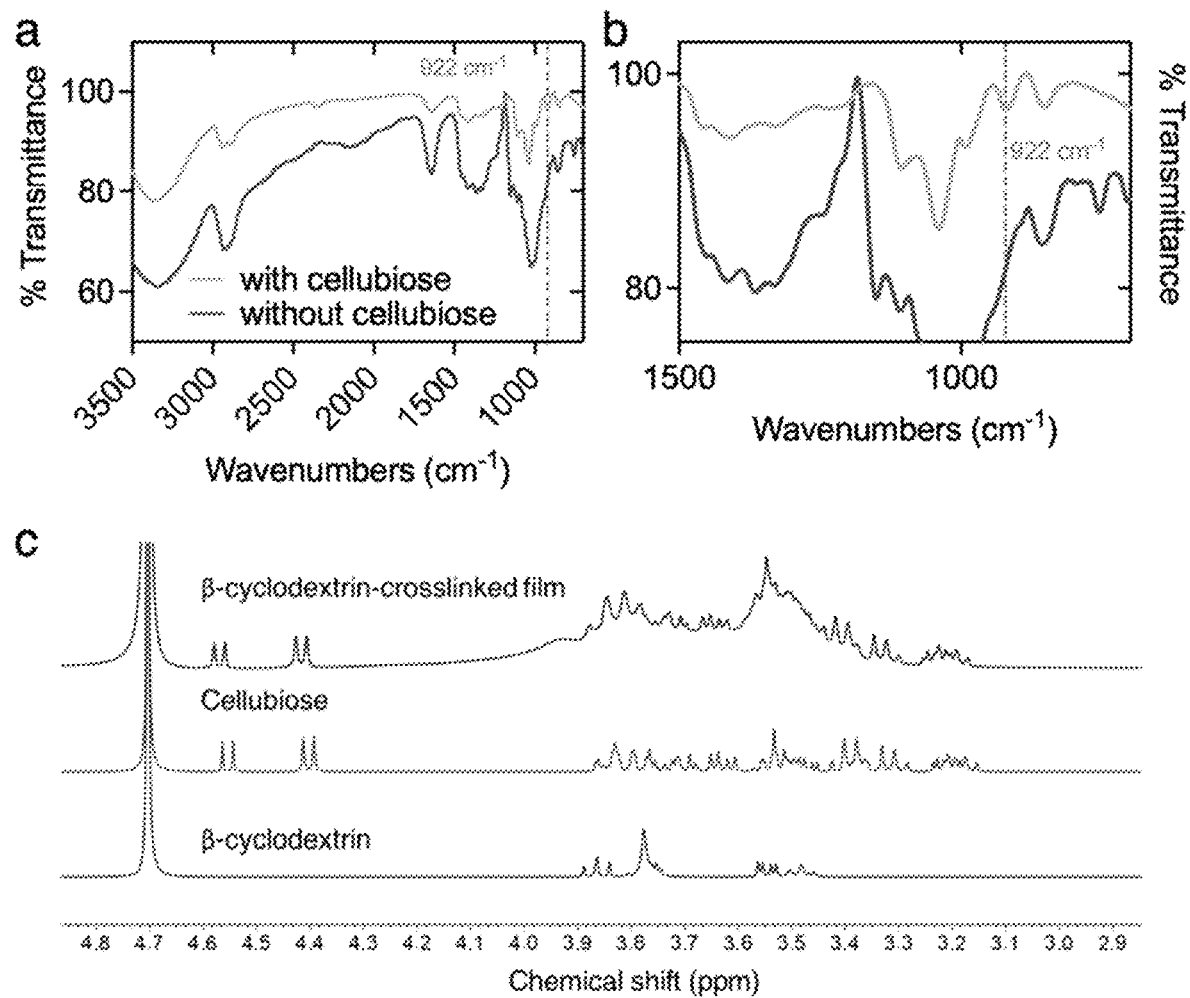
FIG. 4: The characterization of the microbiota responsive polymer film of the invention. a. Infrared spectrogram of the cross-linked products of β-cyclodextrin with cellobiose (purple curve) or without cellobiose (green curve). b. Amplified spectrum in the range of 900 to 1500 $cm^{-1}$ in (a). c. $^1$H-NMR spectrum of β-cyclodextrin crosslinked film (blue), cellobiose (green) and β-cyclodextrin (red) (400 MHz, deuterium oxide).

The infrared spectrum of the film contained the characteristic peak of β-1,4-glucoside bond specific for cellobiose (922 cm$^{-1}$) (FIG. 4a, 4b). At the same time, the $^1$HNMR spectrum of the film material had the characteristic hydrogen spectrum peak of cellobiose (4.41 to 4.58 ppm) (FIG. 4c), indicating that the film contained cellobiose units, which confirmed the successful synthesis of the polymer film.

Figure 5:
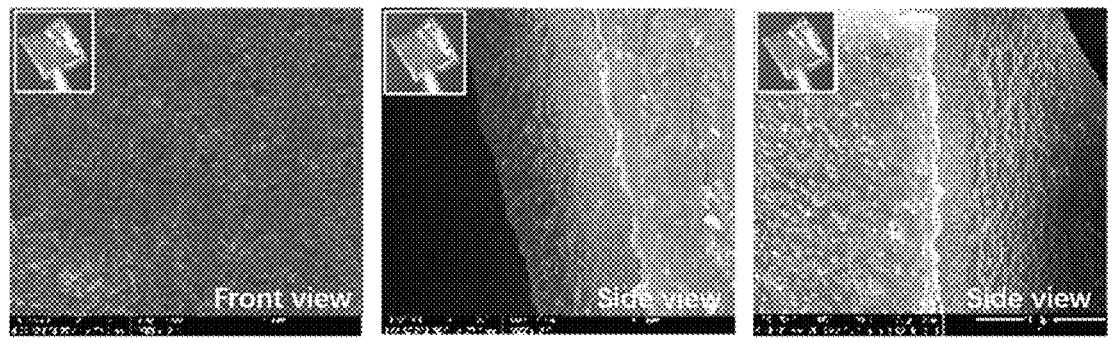
FIG. 5: The microstructure of the polymer film. The surface and cross section structure of the films characterized by scanning electron microscopy; scale, 10 μm.

The microstructure of the obtained films was characterized by scanning electron microscope (SEM). The β-cyclodextrin cross-linked film was fixed on the stage of SEM equipment with conductive adhesive, and then vacuum plating was carried out to make the tested sample conductive. The surface and cross-section morphology of the sample were photographed and analyzed by SEM. Scanning electron microscopy showed that the side view cross-section of the film had obvious cross-linking network structure, indicating that the cross-linking reaction was sufficient; and the front view surface was regular without cracks, indicating that the film maintained good mechanical strength and film forming performance (FIG. 5).

2.3: Evaluation of Acid-Base Stability of Colonic Enzyme Responsive Polymer Film:

In order to test the acid resistance and base resistance of the polymer film, the tested film sample was pasted on the bottom of the Slide-A-Lyzer G2 dialysis chamber. Release indicator Rhodamine B (RhB) was dissolved in a weak acid buffer (sodium acetate buffer, pH 4.0) or a weak base buffer (phosphate buffer, pH 8.0), and then added to the dialysis chamber. 10 mL weak acid or weak base buffer solution was added outside the dialysis chamber as a release medium.

Figure 6:
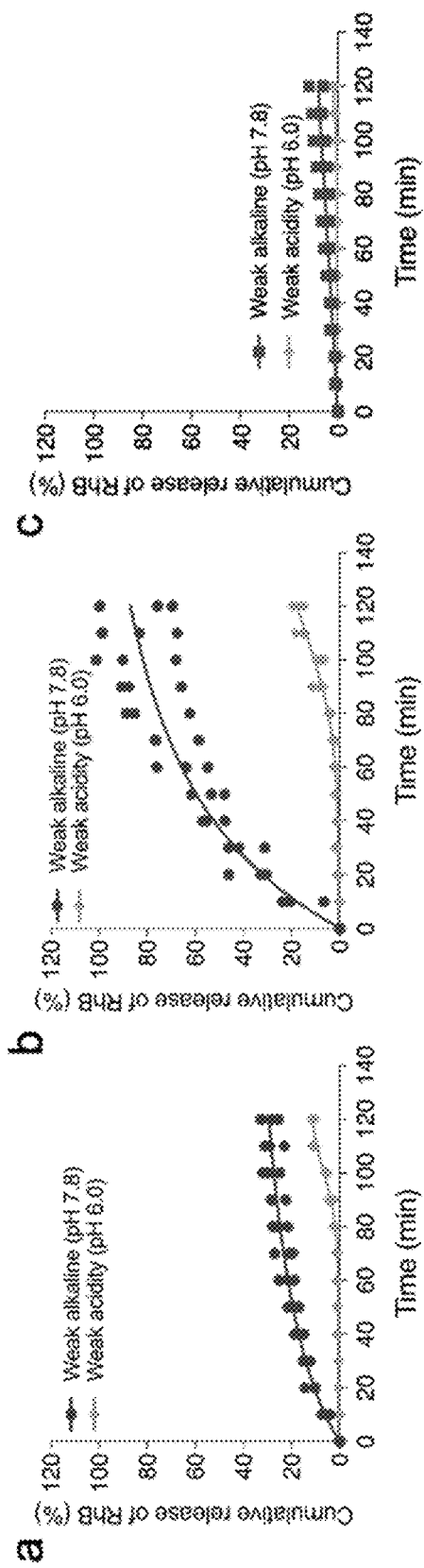
FIG. 6: In vitro release of the microbiota responsive polymer film of the invention in an acid-base environment. a-c, In vitro release results of the films formed with alginate (a), the films formed with chitosan (b) and self-made polymer film (c) in weak alkalinity (pH8.0) and weak acidity (pH4.0). The fluorescence intensity of the released RhB was quantitatively analyzed and normalized with the initial dose as the standard; (n=3).

Compared with the commonly used cross-linked films of sodium alginate and chitosan, the polymer film showed stronger acid-base resistance. The polymer film only released 8.01% and 1.7% in the environment of weak base (blue line, FIG. 6c) and weak acid (yellow line, FIG. 6c) within 2 h (Table 1-3).

TABLE 1

Cumulative release of sodium alginate film in different pH environments

| Time (min) | Cumulative release of sodium alginate film ( %) | | | | | |
|---|---|---|---|---|---|---|
| | In weak base | | | In weak acid | | |
| 0 | 0 | 0 | 0 | 0 | 0 | 0 |
| 10 | 3.916 | 7.482 | 5.457 | 0.136572 | 0.146347 | 0.134355 |
| 20 | 14.555 | 10.473 | 10.479 | 0.275246 | 0.436086 | 0.254786 |
| 30 | 15.276 | 12.353 | 14.066 | 0.573226 | 0.832331 | 0.694793 |
| 40 | 18.808 | 14.984 | 16.582 | 0.730371 | 1.297629 | 0.926391 |
| 50 | 21.576 | 17.055 | 18.578 | 1.021246 | 1.288934 | 1.140199 |
| 60 | 25.411 | 18.931 | 21.637 | 1.081718 | 1.60169 | 1.276998 |
| 70 | 27.142 | 19.677 | 21.191 | 1.128662 | 1.686543 | 1.250457 |
| 80 | 28.083 | 21.612 | 25.596 | 2.705629 | 2.292789 | 2.237262 |
| 90 | 28.491 | 22.584 | 28.518 | 4.00485 | 2.591393 | 4.705554 |
| 100 | 32.153 | 25.045 | 29.875 | 6.115657 | 5.633195 | 4.870542 |
| 110 | 31.223 | 23.173 | 29.235 | 11.52197 | 11.39893 | 9.988709 |
| 120 | 32.881 | 25.681 | 28.761 | 10.57876 | 11.32885 | 11.50719 |

TABLE 2

Cumulative release of chitosan film in different pH environments

| Time (min) | Cumulative release of chitosan film (%) | | | | | |
|---|---|---|---|---|---|---|
| | In weak base | | | In weak acid | | |
| 0 | 0 | 0 | 0 | 0 | 0 | 0 |
| 10 | 20.708 | 23.95 | 6.686 | 0.120715 | 0.126398 | 0.138504 |
| 20 | 30.692 | 32.782 | 46.258 | 0.969925 | 0.129922 | 0.753502 |
| 30 | 46.369 | 31.233 | 42.04 | 1.712061 | 1.45 | 1.230622 |
| 40 | 57.074 | 47.802 | 55.524 | 1.132868 | 1.51661 | 1.374071 |
| 50 | 53.554 | 47.997 | 61.71 | 2.177359 | 1.752868 | 1.59163 |
| 60 | 63.921 | 54.984 | 76.173 | 2.606 | 2.157013 | 2.007654 |
| 70 | 76.678 | 58.704 | 76.798 | 3.278457 | 1.842892 | 2.092222 |
| 80 | 85.436 | 62.457 | 88.921 | 4.687253 | 3.785187 | 5.09549 |
| 90 | 87.886 | 65.999 | 90.774 | 8.647659 | 7.247502 | 11.51879 |
| 100 | 90.264 | 68.192 | 101.329 | 6.684336 | 7.904728 | 9.505565 |
| 110 | 83.301 | 67.627 | 98.826 | 14.70046 | 15.48783 | 18.35748 |
| 120 | 75.862 | 69.773 | 99.964 | 15.10506 | 17.16574 | 19.50945 |

TABLE 3

Cumulative release of microbiota responsive polymer film in different pH environments

| Time (min) | Cumulative release of microbiota responsive polymer film (%) | | | | | |
|---|---|---|---|---|---|---|
| | In weak base | | | In weak acid | | |
| 0 | 0 | 0 | 0 | 0 | 0 | 0 |
| 10 | 0.917 | 1.051 | 0.859 | 0.132821 | 0.115884 | 0.122988 |
| 20 | 1.023 | 1.495 | 1.026 | 0.124523 | 0.158794 | 0.174707 |
| 30 | 3.048 | 2.187 | 3.191 | 0.164932 | 0.187154 | 0.237906 |
| 40 | 1.945 | 3.386 | 1.973 | 0.148961 | 0.164534 | 0.214434 |
| 50 | 2.266 | 4.7 | 2.463 | 0.157941 | 0.252854 | 0.780783 |
| 60 | 3.604 | 5.756 | 3.471 | 0.181243 | 0.262345 | 0.303095 |
| 70 | 3.687 | 6.555 | 3.824 | 0.266494 | 0.262231 | 0.292637 |
| 80 | 3.63 | 7.652 | 3.639 | 0.225744 | 0.364532 | 0.389084 |
| 90 | 4.32 | 8.708 | 4.55 | 0.316564 | 0.598744 | 0.417899 |
| 100 | 5.296 | 10.075 | 5.156 | 0.459444 | 0.580273 | 0.928948 |
| 110 | 6.539 | 10.507 | 6.614 | 0.919343 | 1.69126 | 1.795379 |
| 120 | 6.016 | 11.846 | 6.172 | 1.034602 | 1.749401 | 2.272783 |

2.4: Evaluation of Microbiota Response Specificity Of Colonic Microbiota Responsive Polymer Film:

To test the β-glucosidase response specificity of microbiota responsive polymer film, 20% (w/v) rat colonic homogenate was prepared as a release medium. In the negative control group, 20% (w/v) rat colonic homogenate was pre-added with 50 mM cellobiose to inhibit the activity of β-glucosidase in the release medium. The whole release process was carried out in the shaking table at a constant temperature of 37° C. and an oscillating speed of 100 rpm away from light. 50 μL of the release medium was collected every 10 min, and same volume of the blank release medium was replenished at the same time, and the fluorescence intensity in the release medium was continuously detected until 120 min.

Figure 7:
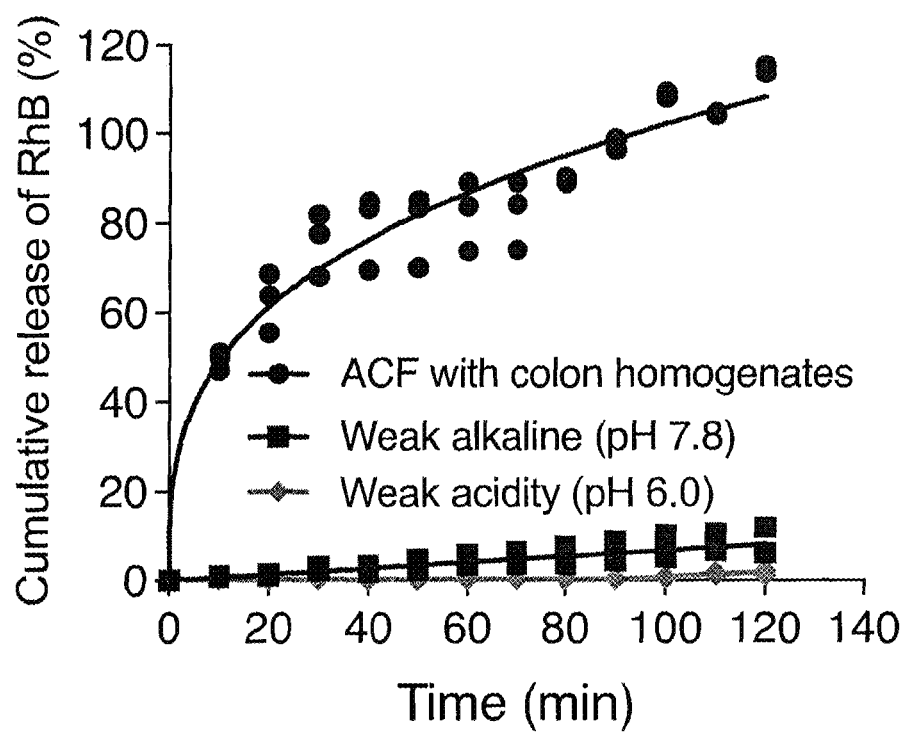
FIG. 7: Characterization of the specific response release of the microbiota responsive polymer film of the invention. In vitro release results of the polymer film of the invention in weakly alkaline (pH7.8), weakly acidic (pH6.0) and weakly alkaline (pH7.8) containing specific enzymes buffer. The fluorescence intensity of the released RhB was quantitatively analyzed with the initial dose as the standard. The structures of the three materials are shown in the figure above (green, new chemical bonds generated after cross-linking; red, β-(1,4)-glycosidic bond for response); (n=3).
Figure 8:
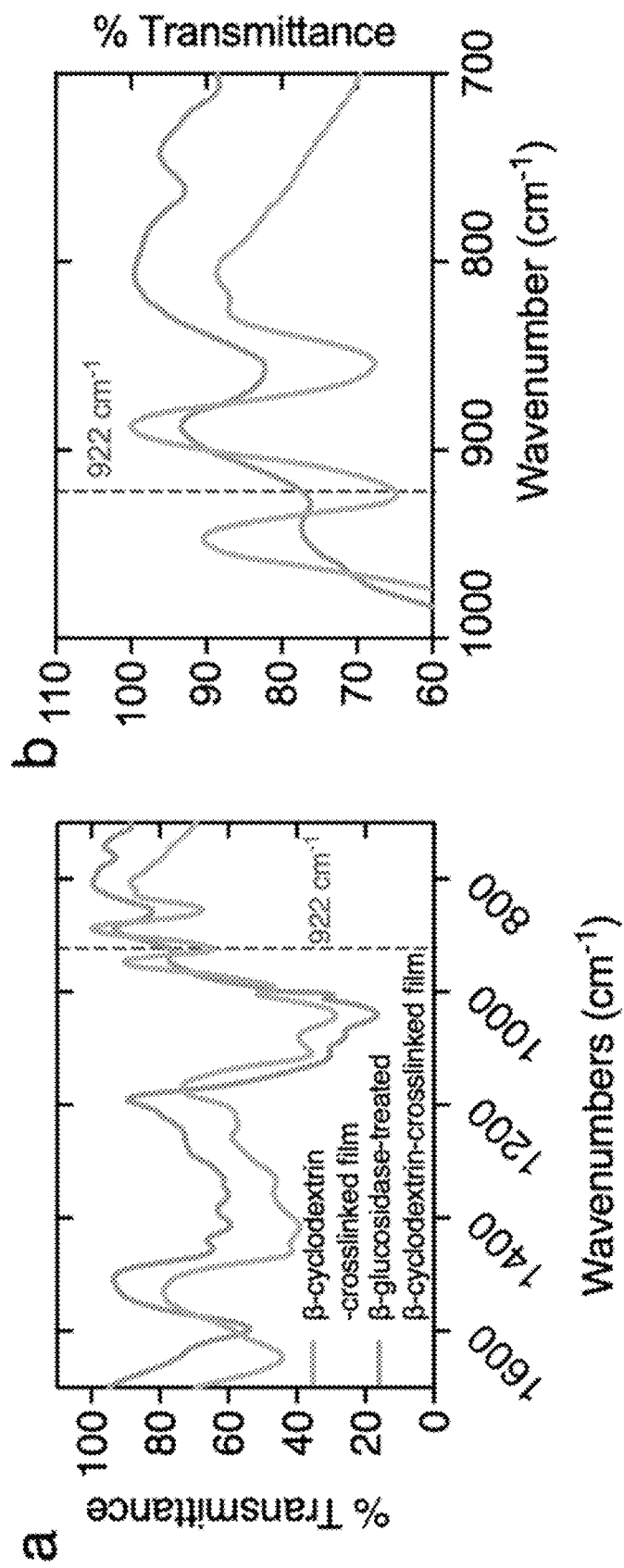
FIG. 8: The infrared spectrum characterization of the microbiota specific response of the microbiota responsive polymer film of the invention. a. Infrared spectrum of the film before and after treatment with β-glucosidase. Dashed line: the characteristic peak of cellobiose at 922 $cm^{-1}$. b. Amplified spectrum of the spectrum (a) in the range of 700 to 1000 $cm^{-1}$.

After β-glucosidase was added in the release medium, 50% of the loaded fluorescent probe was released rapidly within 10 minutes (FIG. 7) (Table 4). Infrared spectrum showed that after coincubation with β-glucosidase, the characteristic peak of β-(1,4)-glucoside bond of β-cyclodextrin crosslinked film at 922 $cm^{-1}$ disappeared (FIG. 8), which indicated that β-cyclodextrin crosslinked film realized the responsive release of β-glucosidase.

TABLE 4

Responsiveness of microbiota responsive polymer film in different solutions

| Time (min) | Cumulative release of colon enzyme responsive polymer films (%) | | | | | | | | |
|---|---|---|---|---|---|---|---|---|---|
| | In weak base | | | In weak acid | | | In artificial colonic fluid + colonic homogenate | | |
| 0 | 0 | 0 | 0 | 0 | 0 | 0 | 0 | 0 | 0 |
| 10 | 0.917 | 1.051 | 0.859 | 0.132821 | 0.115884 | 0.122988 | 47.24412 | 50.19354 | 51.07932 |
| 20 | 1.023 | 1.495 | 1.026 | 0.124523 | 0.158794 | 0.174707 | 68.73864 | 63.86514 | 55.56839 |
| 30 | 3.048 | 2.187 | 3.191 | 0.164932 | 0.187154 | 0.237906 | 77.73902 | 81.93668 | 68.23477 |
| 40 | 1.945 | 3.386 | 1.973 | 0.148961 | 0.164534 | 0.214434 | 84.92002 | 83.36596 | 69.66196 |
| 50 | 2.266 | 4.7 | 2.463 | 0.157941 | 0.252854 | 0.780783 | 85.11979 | 83.41157 | 70.17631 |
| 60 | 3.604 | 5.756 | 3.471 | 0.181243 | 0.262345 | 0.303095 | 89.10877 | 83.77335 | 73.87272 |

TABLE 4-continued

Responsiveness of microbiota responsive polymer film in different solutions

Cumulative release of colon enzyme responsive polymer films (%)

| Time (min) | In weak base | | | In weak acid | | | In artificial colonic fluid + colonic homogenate | | |
|---|---|---|---|---|---|---|---|---|---|
| 70  | 3.687 | 6.555  | 3.824 | 0.266494 | 0.262231 | 0.292637 | 89.14285 | 84.25467 | 74.19623 |
| 80  | 3.63  | 7.652  | 3.639 | 0.225744 | 0.364532 | 0.389084 | 90.285   | 90.285   | 89.004   |
| 90  | 4.32  | 8.708  | 4.55  | 0.316564 | 0.598744 | 0.417899 | 98.724   | 98.724   | 96.348   |
| 100 | 5.296 | 10.075 | 5.156 | 0.459444 | 0.580273 | 0.928948 | 107.994  | 107.994  | 109.014  |
| 110 | 6.539 | 10.507 | 6.614 | 0.919343 | 1.69126  | 1.795379 | 103.959  | 103.959  | 104.547  |
| 120 | 6.016 | 11.846 | 6.172 | 1.034602 | 1.749401 | 2.272783 | 115.302  | 115.302  | 113.484  |

Example 3

Oral Colon-Target Delivery Capsule Prepared by Colonic Microbiota Responsive Polymer Film In this example, a colon-target delivery system prepared by the colonic microbiota responsive polymer film of the invention as a coating material was described taking a capsule dosage form as an example, and its properties were evaluated, and it was used for oral colon-target delivery.

3.1: Preparation and Characterization of Oral Colon-Target Delivery Capsules

Preparation: first, the precursor solution of the microbiota responsive polymer film of the invention was added dropwise into a gelatin capsule shell. A 3D printed metal mold was fixed vertically in the center of the capsule shell with an interval of 300 μm so that the thickness of the precursor solution of the microbiota responsive polymer film (ML for short in the following data display and description) was 300 μm, tolerance was 50 μm, and then solidified in a vacuum drying oven at 65° C. for 12 h. After solidification, the ML was demolded and trimmed. The capsule body and capsule cap were prepared by ML coating using the same process. After the coating preparation of the inner layer of the capsule shell by ML was completed, the delivered diagnostic or therapeutic reagents were charged into the capsule body and capsule cap for pairing and packaging. Furthermore, the pH-responsive layer (PL) (a mixture of talc powder, triethyl citrate and Eudragit 100 with a mass ratio of 1:1:1.5, wherein Eudragit 100 was a commercially available commodity for preparing pH-responsive polymers, and the pH-responsive layer can be coated outside the polymer film of the invention for gastric acid resistance) precursor solution was sprayed on the outer surface of the ML inner layer coated capsule shell by coatiing pan method, and dried to form pH-responsive layer coating (PL for short in the following data display and description, the PL also represented the commonly used oral colon-target delivery dosage form prepared with known polymers). The parameters of the coating pan were set as follows: temperature, 55° C.; air flow rate, 1000 m³/h; spray speed, 0.15 mL/min; atomizing air pressure, 60 pounds per square inch (Psi); rotating speed in the pan, 50 rpm; the inner diameter of the pan 300 mm. After the coating of ML and PL was completed, the resultant was further dried at 65° C. for 15 min to obtain oral colon-target delivery capsules (PL+ML capsules for short in the following data display and description).

Figure 9A:
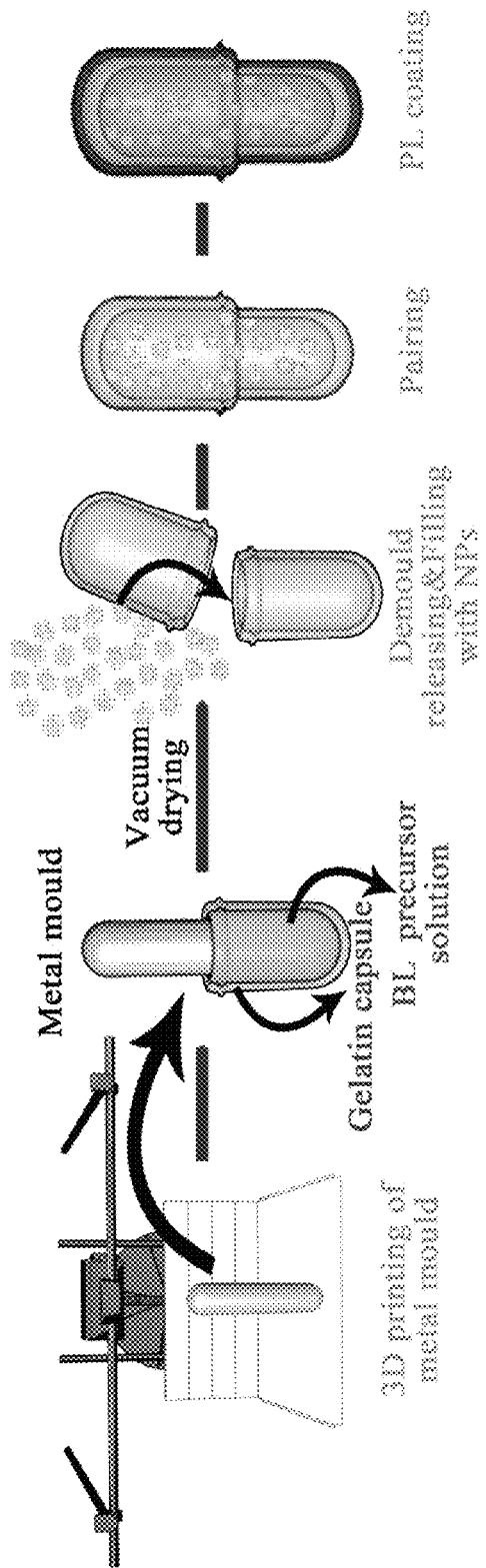
FIG. 9: Preparation and characterization of colon-target delivery capsules (PL+ML capsule for short) coated with the microbiota responsive polymer film of the invention. a. The preparation process of the capsules. The microbiota-responsive layer (ML) is prepared by demolding from a metal mold. After the contents are loaded and the capsule shells are paired, a pH-responsive layer (PL) is coated on the outer surface by coatiing pan method. b. Sectional view of human size capsules obtained according to the preparation method in (a). The 3D structure is displayed by confocal fluorescence z-axis stacking imaging, wherein PL is red and ML is green; scale, 1 mm.
Figure 9B:
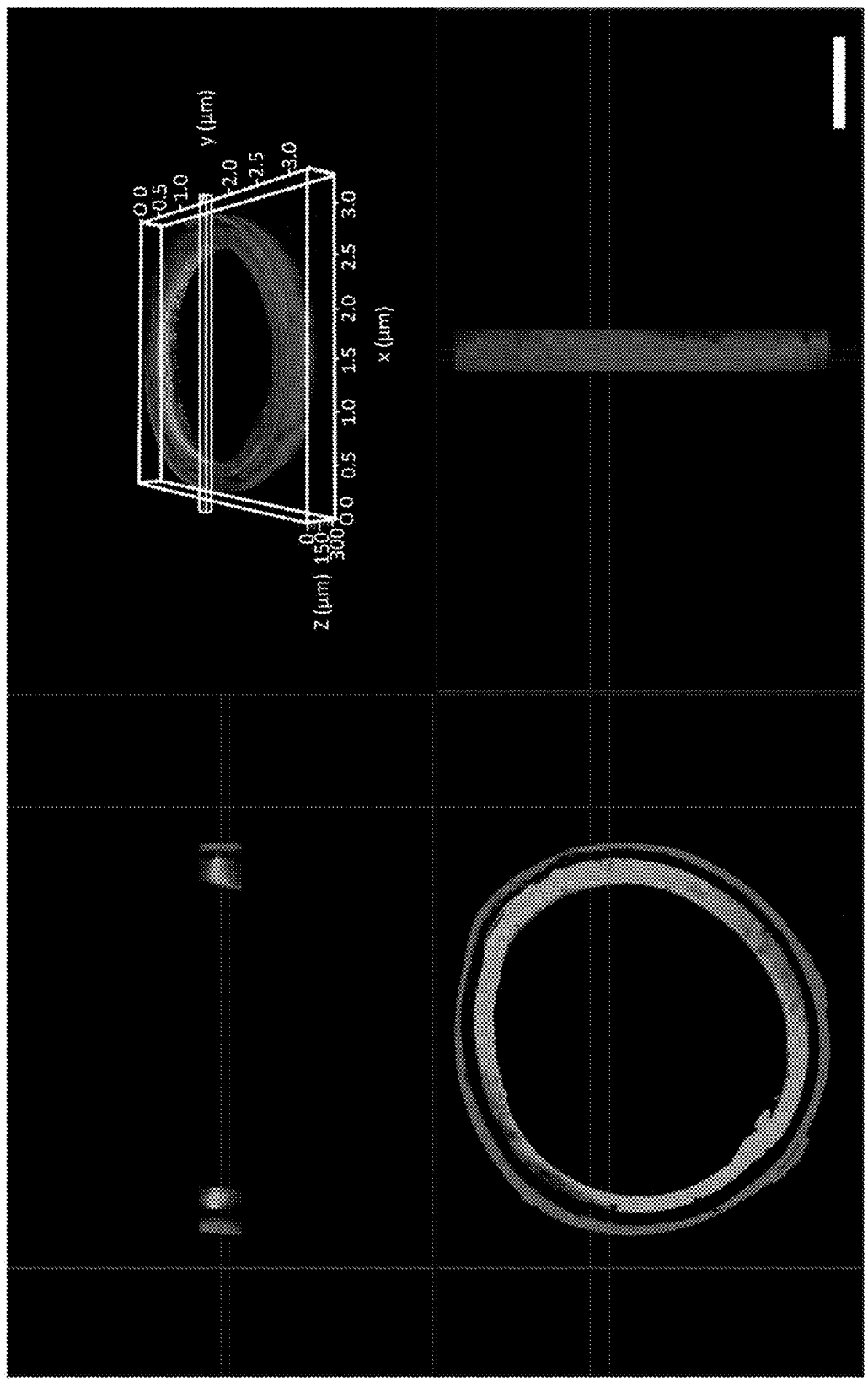

Characterization: In order to characterize the structure of the prepared PL+ML capsules, the PL and ML coatings were labeled with RhB and FITC (fluorescein 5-isothiocyanate) respectively. At the same time, the PL+ML capsule was placed upside down and fixed on the cover glass. The three-dimensional morphology of fluorescent labeled capsules was imaged by confocal laser scanning microscopy at Ex 488/Em 520 nm and Ex 561/Em 605 nm using 10× lens (FIG. 9).

Figure 10:
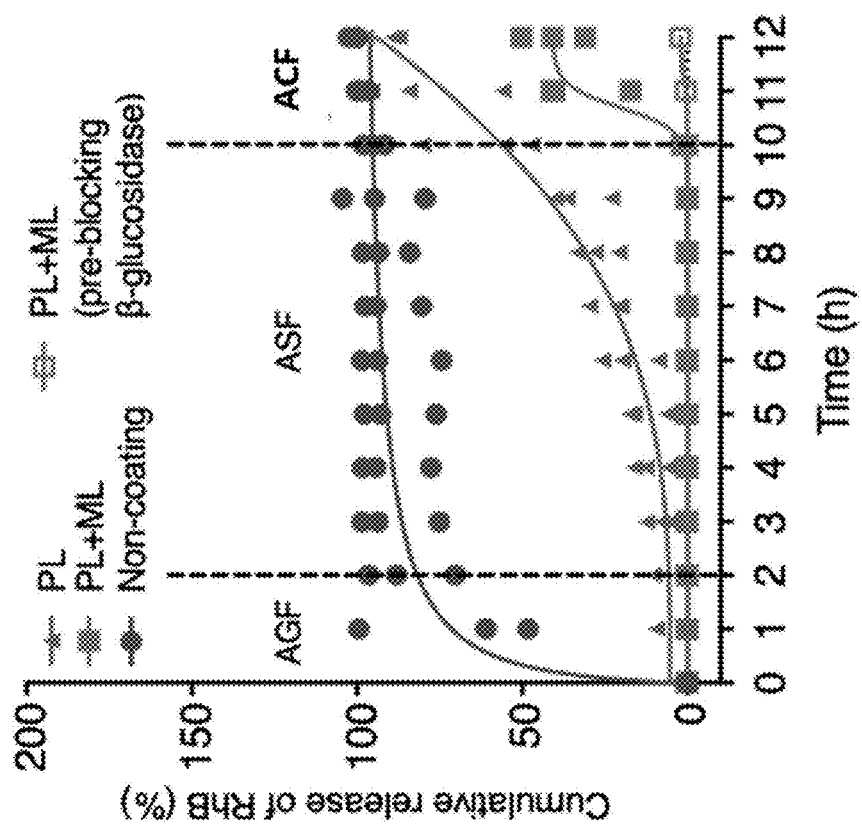
FIG. 10: In vitro release curve of the colon-target delivery capsule (PL+ML capsule for short) of the invention. In vitro β-glucosidase responsive release results of uncoated, PL and PL+ML capsules in an artificial digestive fluid and a soluton containing 20% (w/v) rat colonic homogenate. The release of PL+ML capsules in the release medium presaturated with high concentration cellobiose (blocking β-glucosidase activity) as a control, RhB is encapsulated in the capsule as degradation indicator. The fluorescence intensity of the released RhB was normalized with the initial dose as standard, (n=3).

Step 2: Characterization of Drug Specific Release Outside Oral Colon-Target Delivery Capsules To test the colon-target release property, the capsules loaded with RhB fluorescent indicator were successively immersed in artificial gastric fluids (AGF) (0.1 g pepsin and 0.164 mL diluted hydrochloric acid were dissolved in 10 mL distilled water, pH 1.2), artificial small intestinal fluids (ASF) (50 mM $KH_2PO_4$, 24 mM NaOH, pH 6.8) and artificial colonic fluids (ASF) (5 mM $H_3PO_4$, 4.5 mM NaOH, pH 7.81). The whole release process was carried out in the shaking table at a constant temperature of 37° C. and an oscillating speed of 100 rpm away from light. At a predetermined release time point (1, 2, 3, 4, 5, 6, 7, 8, 9, 10, 11, and 12 h), 200 μL release medium sample was collected for fluorescence quantification. The release medium was replenished at each time point to keep the release test conditions consistent in each time period (FIG. 10) (Table 5). PL capsule represented a commonly used oral colon-target delivery dosage form prepared with known polymers. PL+ML capsule represented an innovative oral colon-target delivery dosage form prepared using the microbiota responsive polymer film of the invention. It can be seen from the data in FIG. 9 that the PL+ML capsule exhibited the stability in artificial gastric fluids and small intestinal fluids, and only released drugs in artificial colonic fluids.

TABLE 5

Responsiveness of colon-target delivery capsules in artificial colonic fluids and colonic homogenates Cumulative release (%)

| Time(h) | Uncoated | | | PL coated capsules | | | PL + ML coated capsules | | | PL + ML capsules (pre-sealed β-glucosidase) | | |
|---|---|---|---|---|---|---|---|---|---|---|---|---|
| 0 | 0.00  | 0.00  | 0.00  | 3.99 | 1.16 | 0.12 | 0.32 | 0.39 | 0.29 | 0.00 | 0.00 | 0.00 |
| 1 | 48.46 | 99.62 | 61.06 | 9.41 | 1.35 | 0.75 | 0.40 | 0.24 | 0.16 | 0.03 | 0.03 | 0.16 |

TABLE 5-continued

Responsiveness of colon-target delivery capsules in artificial colonic fluids and colonic homogenates Cumulative release (%)

| Time(h) | Uncoated | | | PL coated capsules | | | PL + ML coated capsules | | | PL + ML capsules (pre-sealed β-glucosidase) | | |
|---|---|---|---|---|---|---|---|---|---|---|---|---|
| 2 | 70.33 | 88.21 | 96.41 | 10.42 | 2.01 | 2.69 | 0.10 | 0.21 | 0.10 | 0.03 | 0.02 | 0.06 |
| 3 | 75.20 | 93.79 | 98.55 | 12.51 | 5.05 | 7.96 | 0.11 | 0.05 | 0.14 | 0.03 | 0.17 | 0.08 |
| 4 | 77.70 | 94.41 | 98.49 | 16.18 | 5.98 | 12.67 | 0.07 | 0.12 | 0.20 | 0.03 | 0.04 | 0.06 |
| 5 | 76.22 | 92.95 | 97.95 | 17.55 | 6.21 | 16.23 | 0.02 | 0.20 | 0.11 | 0.03 | 0.03 | 0.11 |
| 6 | 74.50 | 93.83 | 98.74 | 25.73 | 8.92 | 19.74 | 0.06 | 0.09 | 0.21 | 0.03 | 0.03 | 0.07 |
| 7 | 80.51 | 94.29 | 97.69 | 29.84 | 21.19 | 20.22 | 0.08 | 0.05 | 0.11 | 0.04 | | 0.05 |
| 8 | 84.16 | 93.49 | 98.39 | 33.35 | 28.02 | 20.80 | 0.03 | 0.02 | 0.10 | 0.04 | 0.83 | 0.05 |
| 9 | 79.58 | 94.90 | 104.48 | 40.13 | 36.51 | 23.11 | 0.02 | 0.02 | 0.11 | 0.03 | 0.22 | 0.48 |
| 10 | 91.74 | 95.17 | 98.12 | 55.55 | 47.14 | 80.20 | 1.28 | 1.28 | 1.83 | 0.03 | 0.09 | 0.09 |
| 11 | 96.69 | 98.98 | 100.30 | 55.95 | 84.34 | 95.75 | 17.37 | 41.22 | 40.38 | 0.61 | 0.47 | 0.53 |
| 12 | 102.69 | 100.22 | 99.92 | 87.45 | 89.13 | 97.69 | 40.88 | 50.29 | 31.08 | 1.22 | 3.12 | 2.08 |

Step 3: Characterization of Drug Specific Release of Oral Colon-Target Delivery Capsules in the Inflammatory Colon Site SPECT/CT imaging was used to trace the release in vivo. PL or PL+ML capsules were labeled with radionuclide $^{99m}$Tc, about 1 mCi of $^{99m}$Tc was mixed with 100 mg dextrin, and then encapsulated in PL and PL+ML capsules. PL capsules represented a commonly used oral colon-target delivery dosage form prepared with known polymers. PL+ML capsules represented an innovative oral colon-target delivery dosage form prepared using the microbiota responsive polymer film of the invention. After oral administration of $^{99m}$Tc labeled PL or PL+ML capsules, SPECT/CT imaging was performed at 1, 6, 15 and 18 h in rats to study the release of the capsules in the digestive tract. SPECT/CT imaging started from 15% window of imaging field of view at 140 KeV power.

Figure 11:
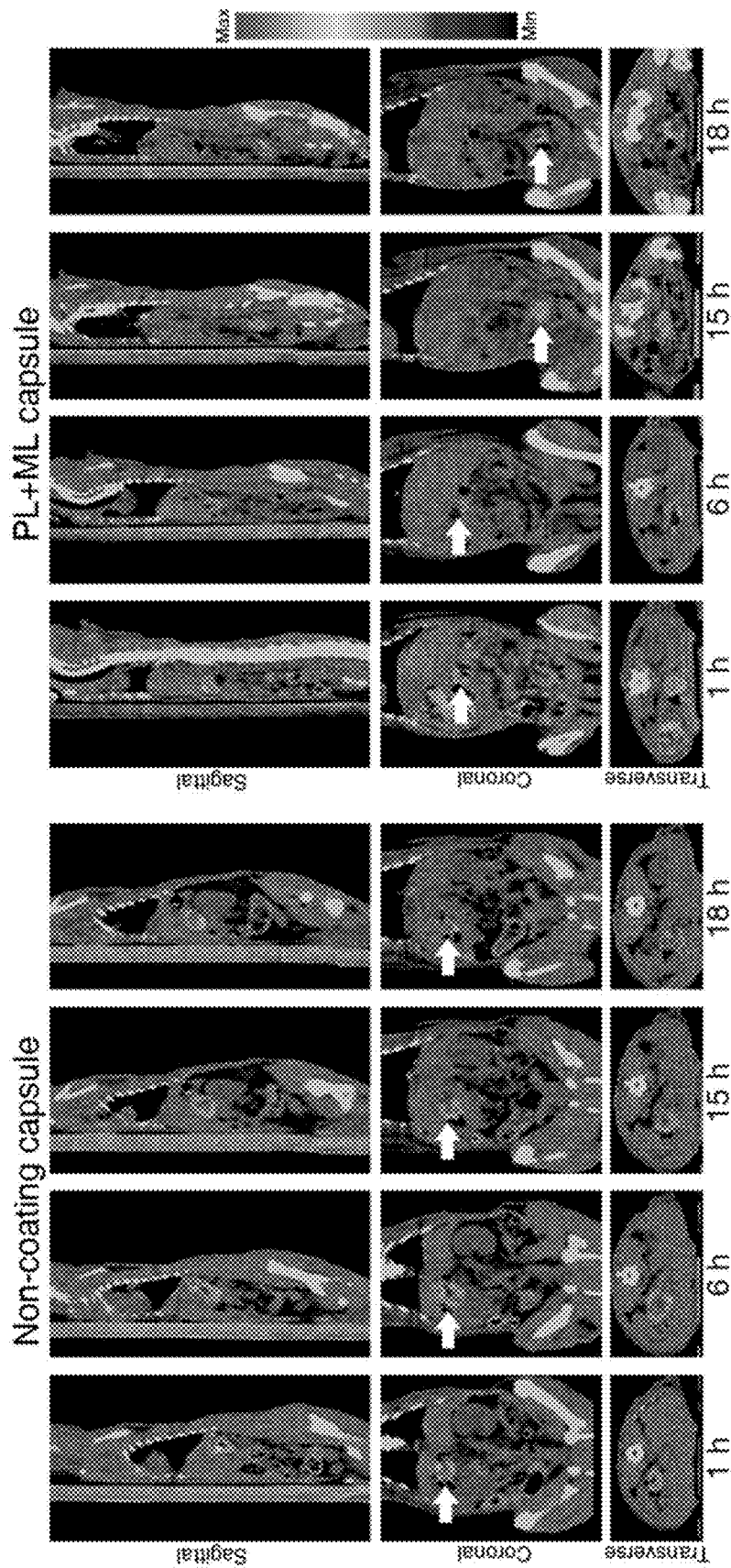
FIG. 11: In vivo imaging confirms the colon-target specificity of the colon-target delivery capsule (PL+ML capsule for short) of the invention. SPECT/CT imaging of rat digestive tract after oral administration of 99 mTc loaded uncoated capsules or PL+ML capsules for 1, 6, 15 and 18 hours. The white arrow is the position of the $^{99m}$Tc signal.

The results showed that PL+ML capsules specifically released in the colon of rats with colitis induced by dextran sulfate sodium (DSS). The release and leakage of PL+ML capsules encapsulated with $^{99m}$Tc in vivo were traced by SPECT imaging. The encapsulated radionuclide $^{99m}$Tc probe was used to indicate the leakage of the capsules. The results showed that the signal of PL capsules group remained in the upper digestive tract all the time, and did not transfer to the colon even after 15 hours, indicating that almost all load probes leaked in the upper digestive tract. In contrast, in PL+ML capsule group, after 15 hours of upper gastrointestinal emptying and transportation, strong signals appeared at the colon, indicating that it delivered the load probe to the colon; and the signal gradually diffused at 18 h, indicating that PL+ML capsules began to release in the colon (FIG. 11).

Figure 12:
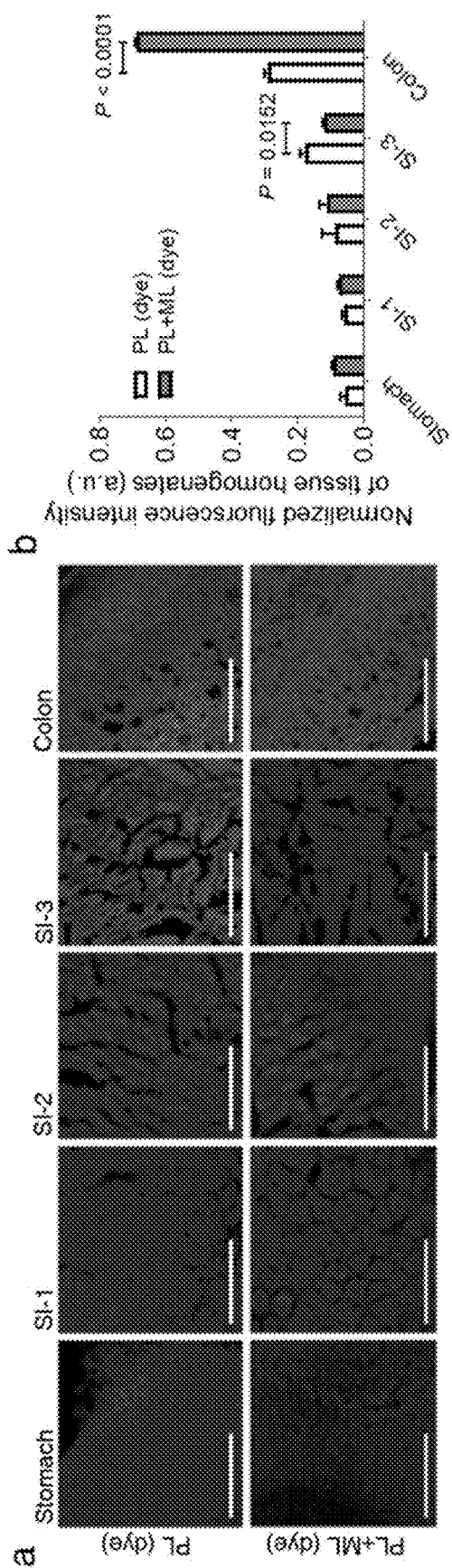
FIG. 12: Tissue level fluorescence imaging confirms the colon specific response release of the colon-target delivery capsule (PL+ML capsule for short) of the invention. a. Confocal fluorescence imaging of stomach, proximal small intestine (SI-1), middle small intestine (SI-2), distal small intestine (SI-3) and colon in colitis rats after oral administration of PL or PL+ML capsule for 18 hours. Scale, 250 μm. b. The fluorescence intensity of each tissue homogenate in (a) figure was quantitatively analyzed by microplate reader, and the data were expressed as mean±standard error (n=3).

The release and distribution of PL+ML capsules in the digestive tract after oral administration were further observed by fluorescence confocal method, and its tissue homogenate was quantified by fluorescence (FIG. 12). Apo 10×/0.4 or Apo 10×/0.7 objective lens were used for imaging, and the images were acquired and analyzed through Leica LAS AF software. The specific parameters of confocal fluorescence imaging were set as follows: RhB (Ex 514 nm/Em 550 nm-570 nm); Texas Red (Ex 561 nm/Em 600 nm-620 nm); 1024×1024 pixel images were scaned at 400 Hz using interframe mode. For IVIS imaging, tissue sections were imaged at Ex 535 nm/Em 600 nm. Fluorescence imaging was obtained and analyzed by Living Imaging software. The fluorescence quantification of tissue homogenate was measured by the microplate reader. The specific parameters of fluorescence quantification were set as follows: RhB (Ex 514 nm/Em 550 nm-570 nm); Texas Red (Ex 561 nm/Em 600 nm-620 nm). The total fluorescence intensity in the homogenates of stomach, small intestine and colon tissues was used to normalize the fluorescence quantitative results of the homogenates.

Figure 13:
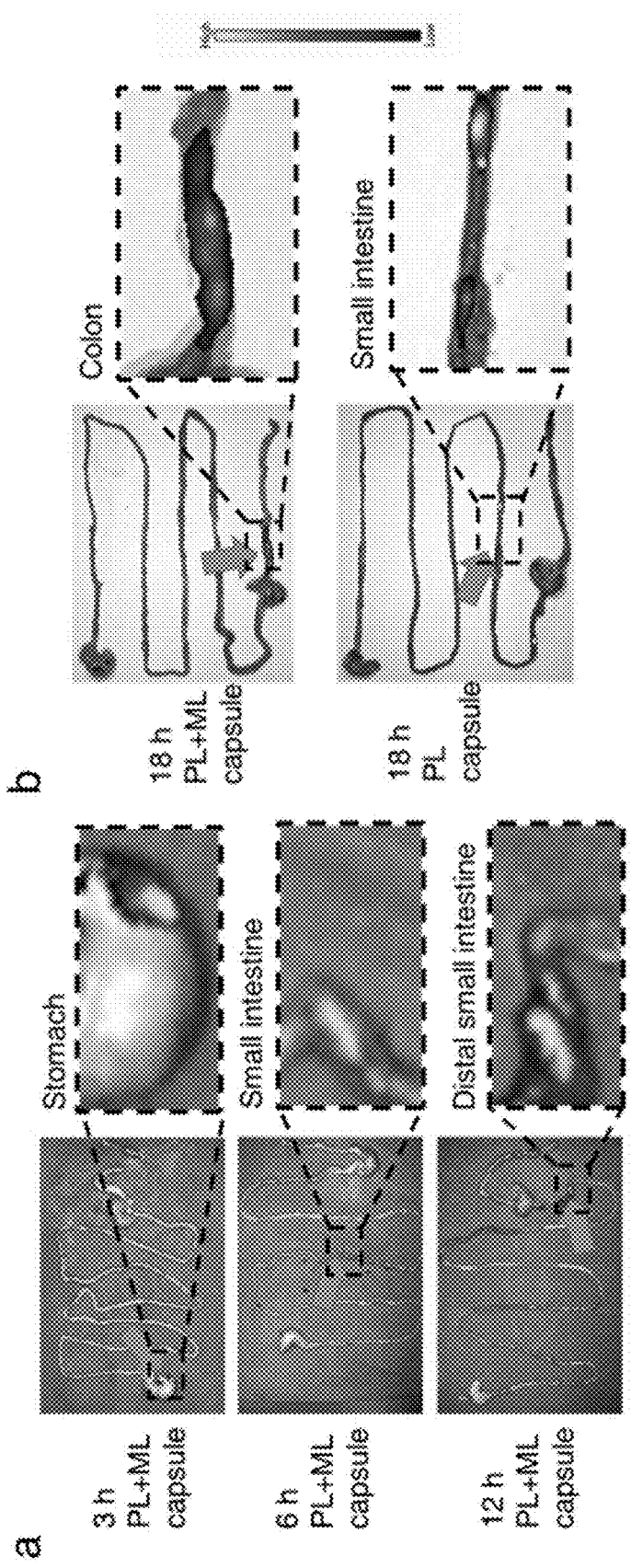
FIG. 13: IVIS image of digestive tract distribution confirms the colon specific response release of colon-target delivery capsule (PL+ML capsule for short) of the invention. The distribution image of PL+ML and PL capsule in the digestive tract of colitis rats. a. IVIS images of digestive tract of colitis rats after oral aministering PL+ML capsules at different time points. The RhB encapsulated PL+ML capsules remained intact before reaching the colon at 3, 6 and 12 hours enlarged image in the dotted box on the right). b. IVIS image of intestinal tract of colitis rats 18 h after aministering RhB encapsulated PL+ML (upper) or PL (lower) capsules (enlarged image in the dotted box on the right). The encapsulated RhB strength is displayed from weak to strong in red to yellow; The green arrow indicates the position of the capsule.

The results showed that the digestive tract of colitis rats was separated at different time points after the fluorescent dye encapsulated PL+ML capsules were orally administered, and the fluorescence distribution in the stomach, proximal small intestine, middle small intestine, distal small intestine and colon was observed. The results showed that the capsules uncoated with microbiota responsive polymer film (PL capsules) showed strong fluorescence signals in the distal small intestine, indicating that pH-responsive coating alone was not enough to avoid leakage in the upper digestive tract (FIG. 12a). However, after taking PL+ML capsules orally, no fluorescence signal was detected in each segment of the small intestine, and only strong fluorescence was observed in the colon segment. The fluorescence quantitative results in the tissue homogenates of various parts of the digestive tract were consistent with the confocal observation. The leakage amount of PL+ML capsules in the upper digestive tract was significantly lower than that of PL capsules, and the release amount in the colon was 1.37 times of that of PL capsules (FIG. 12b). In vitro tissue fluorescence imaging also confirmed that PL+ML capsule was an aggregated capsule signal in the upper digestive tract, indicating that it remained intact without leakage; It was shown as diffuse signal after 18 h, indicating its degradation and release in colon (FIG. 13).

Experimental Example 1

Oral Colon-Target Delivery Capsule Prepared with Microbiota Responsive Polymer Film Achieved Specific Release in Colonic Fluids Samples of Clinical Patients In this experimental example, the specific drug release of oral colon-target delivery capsule (PL+ML capsule) in the colonic fluids of clinical patients was taken as an example to show that the oral colon-target delivery system prepared with the microbiota responsive polymer film of the invention as the coating material can achieve: 1) effective protection of the delivered drugs in gastric fluids and small intestine fluids, and 2) efficient release of the delivered drugs in colonic fluids, which verified the specific response of the delivery system to human colonic fluids.

Step 1: Evaluation of Drug Release of Oral Colon-Target Delivery Capsules Prepared with Colonic Bacteria Enzyme Responsive Polymer Film in Human Gastric Fluids, Small Intestine Fluids and Colonic Fluids The in vitro digestive fluids release test of the capsule was conducted in a release medium composed of 15 mL human digestive tract fluids, and the release medium was replenished at each time point to maintain the release conditions. First, 1 mg RhB was encapsulated in the capsule as the release indicator, then the capsule was put into 15 mL of release medium, finally the release device was placed in the shaking table and shaken at 100 rpm, and kept away from light at 37° C. The incubation time and sequence of capsules with different release media were as follows: capsules were incubated with patients' gastric fluids (patients 1-5) for 2 hours, intestinal fluids (patients 6-10) for 8 hours, and colonic fluids (patients 11-15) for 2 hours. In each clinical sample group, the sequential release of three capsules in gastric fluids, intestinal fluids and colonic fluids was tested in parallel. At a predetermined time point (1, 2, 3, 4, 5, 6, 7, 8, 9, 10, 11, and 12 h), 200 µL release medium samples were collected for quantification.

Figure 14:
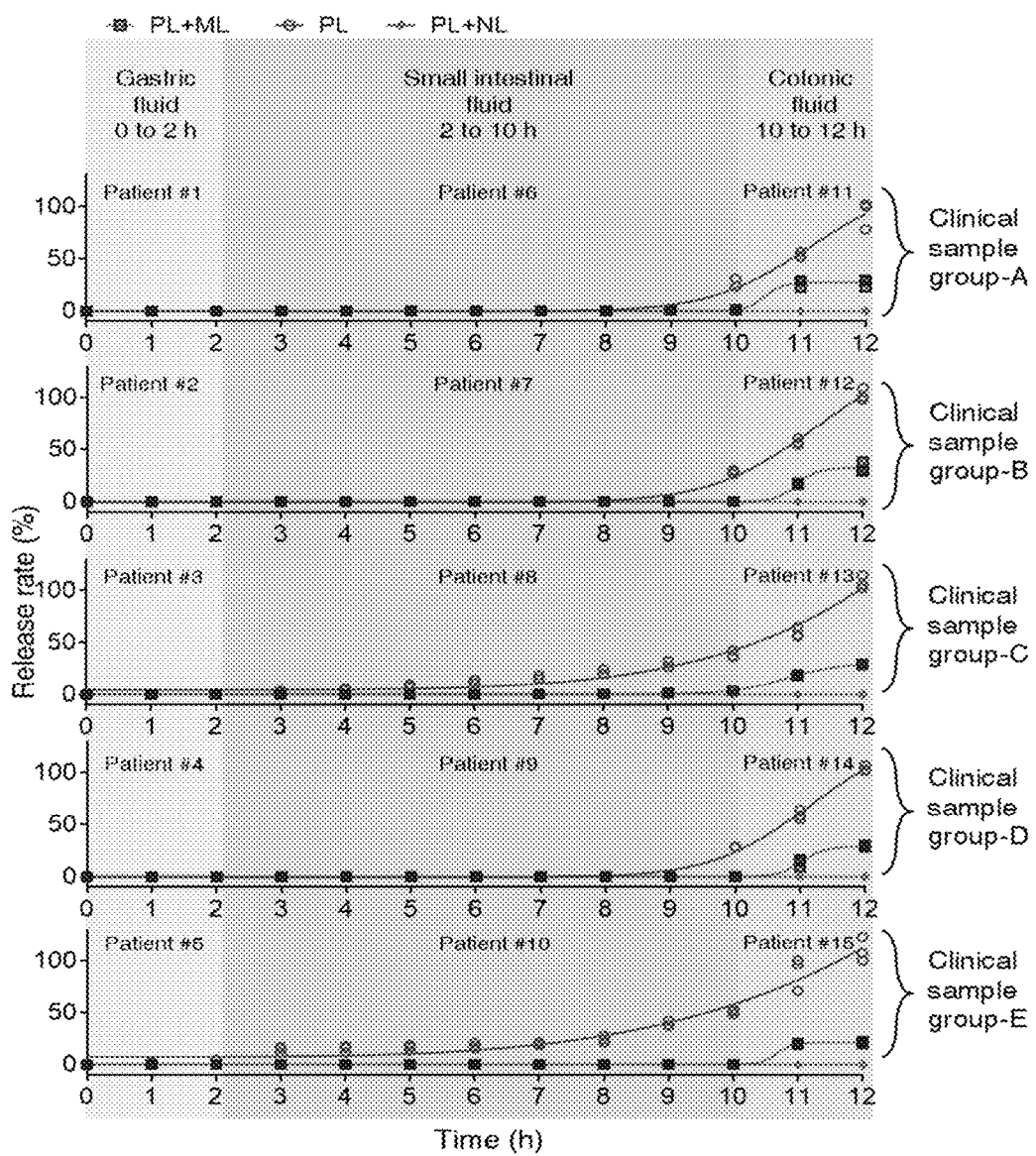
FIG. 14: Evaluation of the colitis-target release capacity of the colon-target delivery capsule (PL+ML capsule for short) of the invention by using the patient's digestive tract fluid. The cumulative release amount of PL, PL+ML or PL+NL capsules after culturing in gastric fluid from 0 h to 2 h, in intestinal fluid from 2 h to 10 h, and in colonic fluid from 10 h to 12 h, respectively. Digestive tract fluid was collected from patients 1-15.
Figure 15:
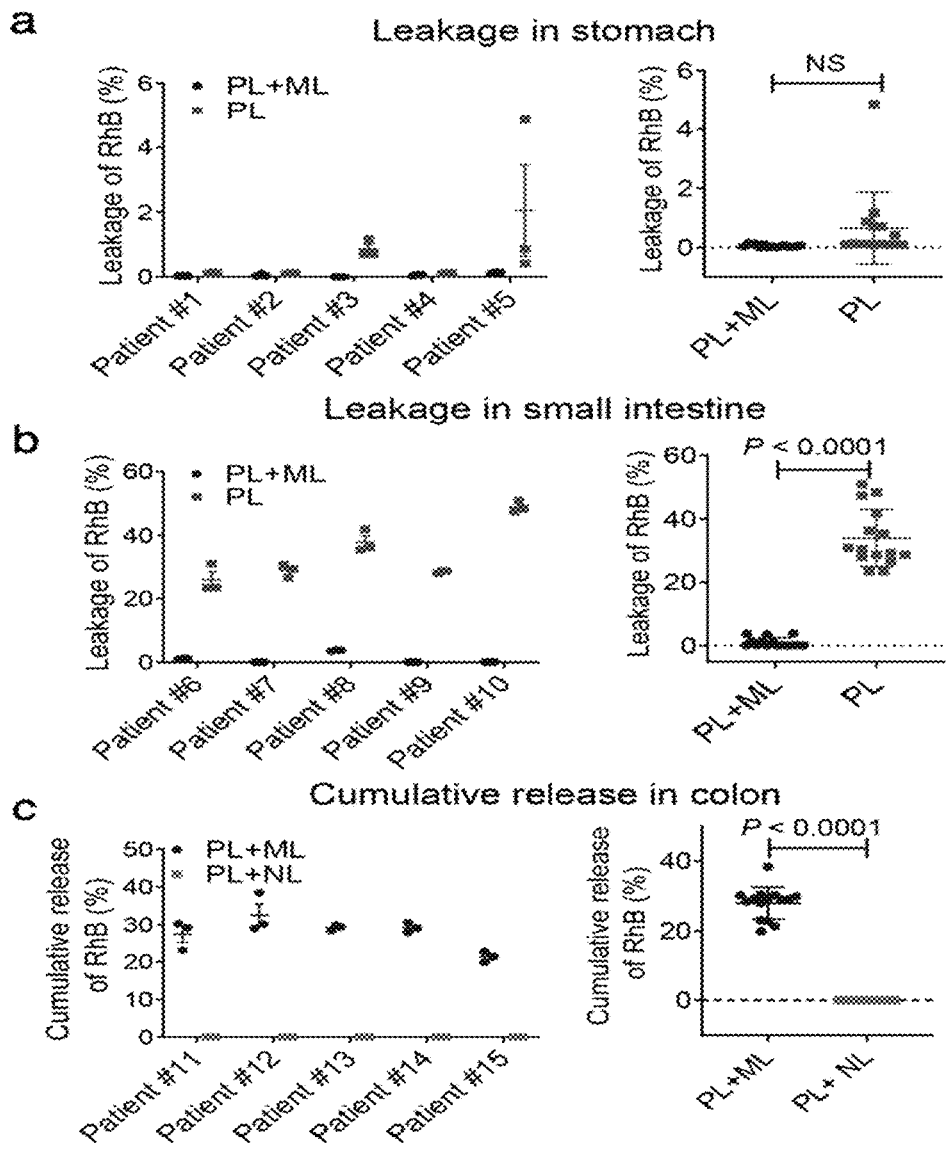
FIG. 15: Statistical analysis of colon-target release capacity of the colon-target delivery capsule (PL+ML capsule for short) of the invention in patients' digestive tract fluid. RhB is encapsulated in capsules as a release indicator. a.b. Premature leakage of PL capsule and PL+ML capsule in gastric fluid (a) of patients 1-5 and intestinal fluid (b) of patients 6-10. For a, b and c in the left figure, three parallel measurements were made for each sample. For a, b and c in the right figure, the P value is shown on the chart; NS, no significant difference; Unpaired bilateral t-test; The data are expressed as mean±standard error (n=15).

It can be seen from FIG. 14 and FIG. 15 that PL capsules uncoated with microbiota responsive polymer film leakd a lot in gastric fluids and small intestinal fluids, so that the capsules continued to release in colonic fluids, and thus the specific release degree in colon cannot be characterized; however, PL+ML capsules coaed with microbiota responsive polymer film retained the loaded fluorescent indicator in the capsule, and there was almost no leakage in the intestinal fluids, but only specifically released in the colonic fluids.

Step 2: Comparison of Drug Release in Human Colonic Fluids Between Oral Colon-Target Delivery Capsules Prepared by Colonic Microbiota Responsive Polymer Films and Oral Capsules Prepared by Non-Microbiota Responsive Polymer Films In order to further evaluate the responsive release of enzymes in colonic fluids of patients with oral colon-target delivery capsules prepared by the microbiota responsive polymer films, a film coat consisting of the non-responsive layer (NL) of PL and β-glucosidase was prepared as a negative control. The NL layer was prepared from nitrocellulose, with strength equivalent to ML but no colonic microbiota response. Compared with PL+NL capsules, the release of PL+ML capsules was significantly increased in colonic fluids of patients. PL+ML showed significant responsive release in colonic fluids, and about 30% of the loaded fluorescent indicator was released accumulatively within 2 hours, while PL+NL showed passivity without significant release (FIG. 15c). This indicated that the β-enzyme responsive release of the polymer was still effective in the colon environment of patients with IBD.

In this experiment, the drug release test of oral colon-target delivery capsules prepared by colonic microbiota responsive polymer films in colonic fluid samples of clinical patients was carried out. The results showed that the delivery system could ensure the specific release of drugs in the colon while not leaking in the gastric and intestinal fluids. Since the gastric fluids, colonic fluids and small intestine fluids used were all human samples, this delivery system has great clinical application potential.

Experimental Example 2

Application of Oral Colon-Target Delivery Capsules Prepared by the Colonic Microbiota Responsive Polymer Films in the Treatment of Colon Diseases In this experimental example, acute colitis was used as a disease model, and the therapeutic application of oral colon-target delivery capsules (PL+ML capsules) prepared by colonic microbiota responsive polymer films on colon diseases was carried out. This confirmed the advantages of the capsules in the treatment of colon diseases compared with the commonly used oral colon-target delivery capsules (PL capsules) prepared with known polymers.

Step 1. Construct DSS Induced Rat Acute Colitis Disease Models and Determine Treatment Schemes Construction of DSS induced rat acute colitis model: the DSS induced acute colitis model was constructed by administering a drinking water containing 6.5% (w/v) DSS to SD rats for 11 consecutive days.

Figure 16:
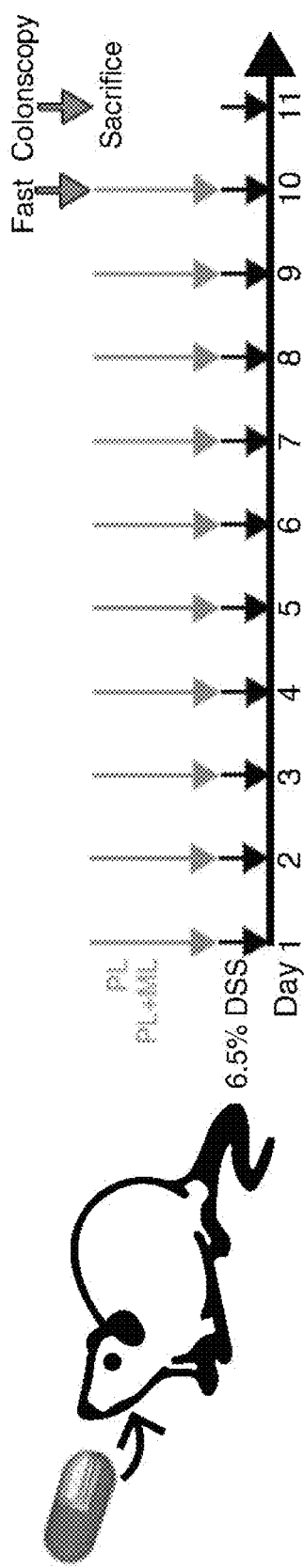
FIG. 16: Therapeutic scheme of the colon-target delivery capsule (PL+ML capsule for short) of the invention for DSS induced acute colitis rats. PL and PL+ML groups were administered with PL capsules and PL+ML capsules loaded with 5-ASA (2.5 mg/kg) every day within 10 days, respectively. In the control group, untreated colitis rats (DSS) and healthy rats (Healthy) were administered with blank gelatin capsules.

Treatment and administration schemes of DSS induced acute colitis rats: treatment started from the first day after DSS feeding. The experiment was divided into DSS group, PL group and PL+ML group. The specific drug dose setting and administration scheme were as follows (FIG. 16): (i) DSS group (blank gelatin capsule); (ii) PL group (PL capsule containing 2.5 mg/kg free 5-ASA, once a day); (iii) PL+ML group (PL+ML containing 2.5 mg/kg free 5-ASA, once a day).

During the experiment, the test animals were randomly assigned to each experimental groups. All enema operations were performed in a horizontal posture to imitate the commonly used clinical enema posture. The rats were fasted for 12 hours before colonoscopy on the 11th day, and then killed for subsequent analysis.

During the experiment, the experimental animals were randomly assigned to each experimental group. All enema operations were performed in a horizontal posture to imitate the commonly used clinical enema posture. The rats were fasted for 12 hours before colonoscopy on the 11th day, and then killed for subsequent analysis.

Step 2. Evaluation of Therapeutic Effect of Oral Colon-Target Delivery Capsules Prepared by Colonic Microbiota Responsive Polymer Films on DSS Induced Acute Colitis In Rats The therapeutic effect of colitis in rats was evaluated by endoscopic manifestations and pathological staining. The therapeutic effect of colonic microbiota responsive film coated capsules group on colitis in rats was significantly improved compared with pH sensitive layer coated capsules group.

Figure 17:
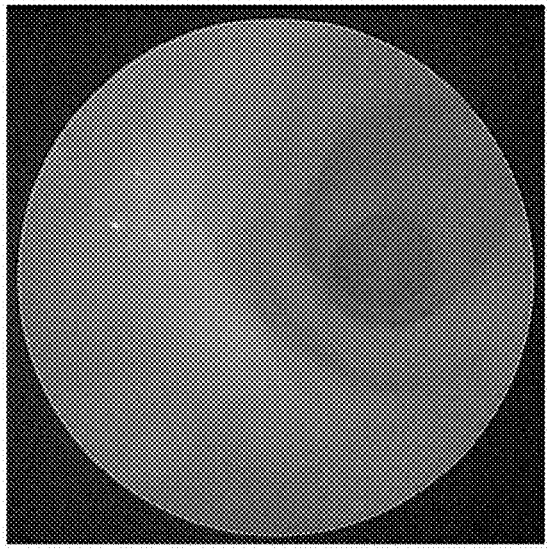
FIG. 17: Evaluation of the therapeutic effect of the colon-target delivery capsule (PL+ML capsule for short) of the invention on DSS induced acute colitis in rats by colonoscopy.
Figure 17:
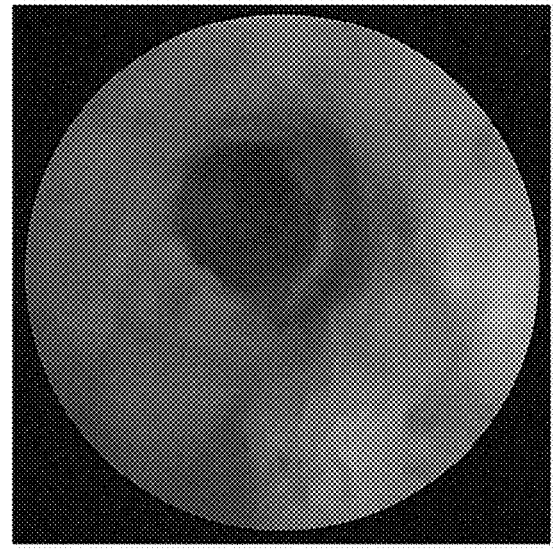
Figure 17:
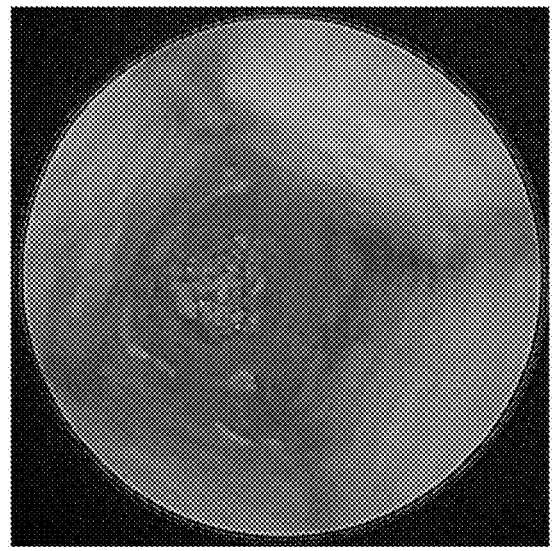
Figure 17:
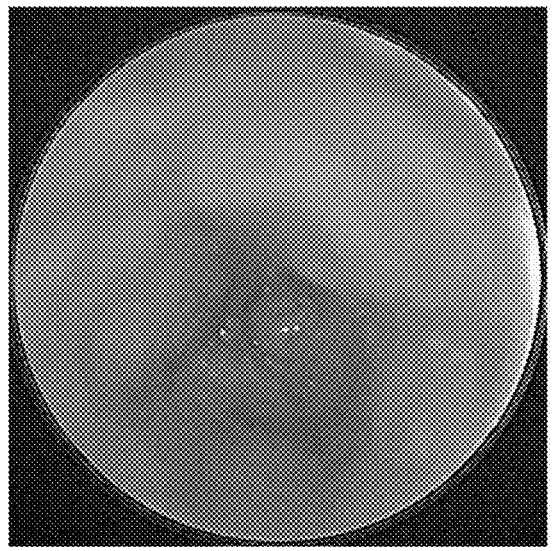
Figure 18:
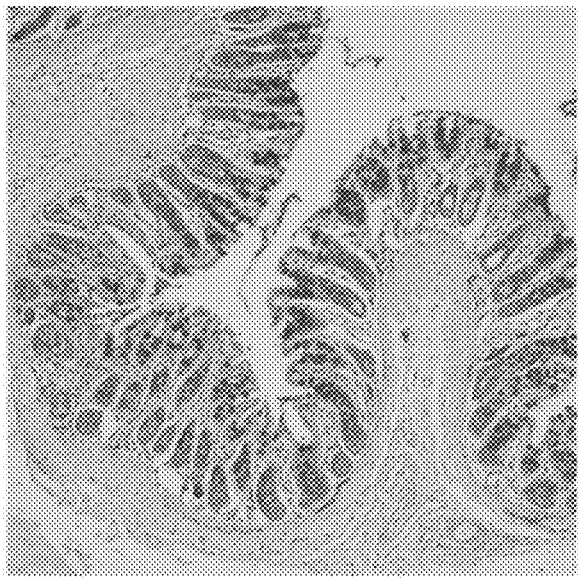
FIG. 18: Evaluation of the therapeutic effect of colon-target delivery capsule (PL+ML capsule for short) of the invention on DSS induced acute colitis in rats by PAS staining pathological section. Scale, 100 μm.
Figure 18:
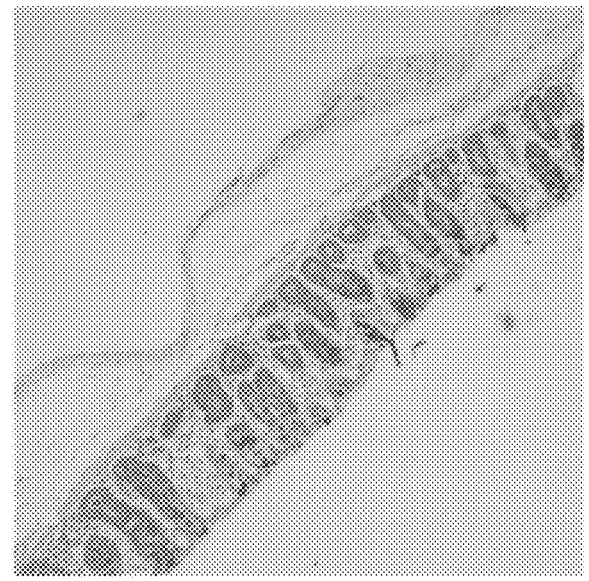
Figure 18:
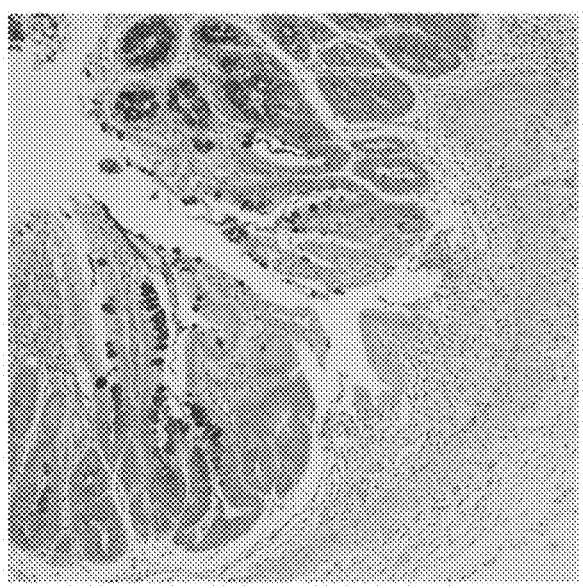
Figure 18:
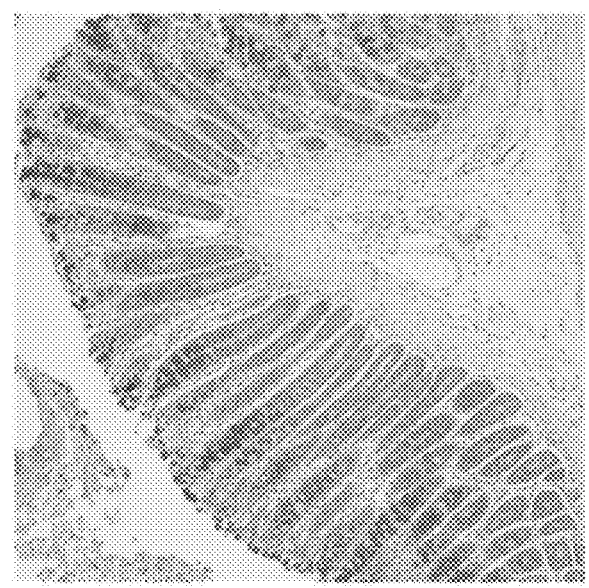
Figure 19:
FIG. 19: Evaluation of the therapeutic effect of the colon-target delivery capsule (PL+ML capsule for short) of the invention on DSS induced acute colitis in rats by H&E staining (hematoxylin-eosin staining) pathological section. Scale, 100 μm.
Figure 19:
Figure 19:
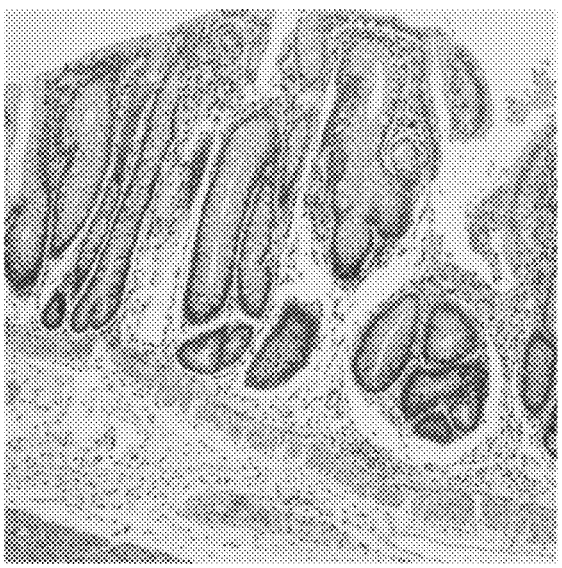
Figure 19:

In DSS and PL groups, there were obvious bleeding spots and defective mucosa, indicating diffuse severe inflammation; PL+ML group showed regular colonic folds with complete mucosal coverage (FIG. 17). Representative periodic acid-schiff stain (PAS) results (FIG. 18) showed that compared with other treatments, PL+ML significantly restored more particles containing PAS positive staining (dyed purple), indicating that it promoted mucin secretion of goblet cells. Representative hematoxylin-eosin (HE) staining results (FIG. 19) showed that the inflammatory infiltration in the lamina propria of PL+ML group was reduced, and the degree of crypt deformation was reduced.

In this experimental example, the application of oral colon-target delivery capsules prepared by colonic microbiota responsive polymer films in the treatment of colitis diseases was carried out. The experimental results showed that the therapeutic effect of the oral colon-target delivery capsule on acute colitis in rats was better than other capsules uncoated with microbiota responsive polymer film, which confirmed the advantages of the oral colon-target delivery capsule in the treatment of colon diseases.

The above are only some embodiments of the invention. Some deformations and improvements can be made by those skilled in the art without departing from the inventive concept of the invention, which all fall within the protection scope of the invention.

The invention claimed is:

1. A colonic microbiota responsive polymer characterized in that it is prepared by the polymerization of a response monomer and a linking monomer, wherein the response monomer is a cellobiose with a β-(1,4)-glucoside bond or/and a lactose with a β-galactoside bond, wherein the linking monomer is γ-cyclodextrin, β-cyclodextrin or hydroxypropyl-β-cyclodextrin, wherein a single or multiple units of the response monomer are connected by a crosslinking agent to a single or multiple units of the linking monomer, and the crosslinking agent is epichlorohydrin.

2. The colonic microbiota responsive polymer according to claim 1, which degrades in response to a high abundance of β-glucosidase and/or β-galactosidase in colon.

3. The colonic microbiota responsive polymer according to claim 1, which is characterized in that the degree of polymerization of the response monomer is 20 to 80; the degree of polymerization of the linking monomer is 20~50.

4. The colonic microbiota responsive polymer according to claim 3, which is characterized in that the degree of polymerization of the response monomer is 30 to 40; the degree of polymerization of the linking monomer is 20~30.

5. The colonic microbiota responsive polymer according to claim 1, which is characterized in that a feeding mass ratio of the response monomer and the linking monomer in the polymerization is not less than 1:5.

6. A method of preparing the colonic microbiota responsive polymer of claim 1, characterized in that the response monomer and the linking monomer is polymerized in an alkaline solution, wherein the polymerization is carried out in the presence of a crosslinking agent, and wherein the crosslinking agent is epichlorohydrin.

7. The method according to claim 6, wherein the reaction temperature of the polymerization is 40-60° C.

8. The method according to claim 6, wherein the polymerization reaction is carried out under the protection of nitrogen.

9. A β-glucosidase or/and β-galactosidase responsive polymer film comprising the polymer of claim 1.

10. A method for preparing the polymer film of claim 9, characterized in that a solution of the colonic microbiota responsive polymer or its mixture with one or more pharmaceutically acceptable excipients is formed into a film by solvent evaporation, phase transfer or chemical crosslinking.

11. The method of preparing the polymer film according to claim 10, wherein the one or more pharmaceutically acceptable excipients are selected from the group consisting of ethyl cellulose, hydroxypropyl methyl cellulose, chitosan, polyethylene glycol and polyvinyl alcohol.

12. The method of preparing the polymer film according to claim 11, wherein the one or more pharmaceutically acceptable excipients is polyvinyl alcohol.

13. An oral colon-targeting delivery system comprising the polymer film as claimed in claim 9.

14. The oral colon-targeting delivery system, which is a capsule.

* * * * *